(12) United States Patent
Acosta et al.

(10) Patent No.: US 11,504,015 B2
(45) Date of Patent: Nov. 22, 2022

(54) METHOD OF PREDICTING FLUID RESPONSIVENESS IN PATIENTS

(71) Applicant: Baylor College of Medicine, Houston, TX (US)

(72) Inventors: Sebastian Acosta, Houston, TX (US); Mubbasheer Ahmed, Houston, TX (US); Suellen Yin, Houston, TX (US); Kenneth M. Brady, Houston, TX (US); Daniel J. Penny, Houston, TX (US); Craig Rusin, Houston, TX (US)

(73) Assignee: Medical Informatics Corp., Houston, TX (US)

( * ) Notice: Subject to any disclaimer, the term of this patent is extended or adjusted under 35 U.S.C. 154(b) by 113 days.

(21) Appl. No.: 16/791,722

(22) Filed: Feb. 14, 2020

(65) Prior Publication Data
US 2020/0260969 A1  Aug. 20, 2020

Related U.S. Application Data

(60) Provisional application No. 62/805,696, filed on Feb. 14, 2019.

(51) Int. Cl.
*A61B 5/024* (2006.01)
*A61B 5/0205* (2006.01)
(Continued)

(52) U.S. Cl.
CPC ........ *A61B 5/02405* (2013.01); *A61B 5/0205* (2013.01); *A61B 5/02225* (2013.01); *A61B 5/145* (2013.01); *A61B 5/7203* (2013.01); *A61B 5/7257* (2013.01); *A61B 5/7275* (2013.01); *A61B 5/742* (2013.01)

(58) Field of Classification Search
CPC .............. A61B 5/02405; A61B 5/0205; A61B 5/02225; A61B 5/145
See application file for complete search history.

(56) References Cited

U.S. PATENT DOCUMENTS 7,850,617 B2  12/2010  Goedje et al.
8,298,151 B2  10/2012  Riobo Aboy et al.
(Continued)

FOREIGN PATENT DOCUMENTS

JP  2006526460 A  11/2006
JP  2015205187 A  11/2015
(Continued)

OTHER PUBLICATIONS

McNames et al., "Statistical Modeling of Cardiovascular Signals and Parameter Estimation Based on the Extended Kalman Filter", Jan. 2008, IEEE Transactions of Biomedical Engineering, vol. 55, No. 1 (Year: 2008).*
(Continued)

*Primary Examiner* — Lynsey C Eiseman
*Assistant Examiner* — Jessica L Mullins
(74) *Attorney, Agent, or Firm* — Schafer IP Law

(57) ABSTRACT

A technique for predicting fluid responsiveness in a critically ill patient comprises measuring physiological data of the patient, then generating an estimate of pulse pressure variability from a Fourier transform of the physiological waveform. Both invasive and non-invasive physiological data measurements may be used.

16 Claims, 13 Drawing Sheets

(51) Int. Cl.
  *A61B 5/022* (2006.01)
  *A61B 5/145* (2006.01)
  *A61B 5/00* (2006.01)

(56) References Cited

U.S. PATENT DOCUMENTS

| | | | |
|---|---|---|---|
| 8,529,458 | B2 | 9/2013 | Kim et al. |
| 8,532,754 | B2 | 9/2013 | Cannesson |
| 9,060,745 | B2 | 6/2015 | Su et al. |
| 9,402,573 | B2 | 8/2016 | Su et al. |
| 9,763,585 | B2 | 9/2017 | Addison et al. |
| 10,328,202 | B2 | 6/2019 | Doyle et al. |
| 10,448,851 | B2 | 10/2019 | Addison et al. |
| 10,499,835 | B2 | 12/2019 | Addison et al. |
| 2008/0033306 | A1 | 2/2008 | Joeken |
| 2009/0048527 | A1 | 2/2009 | Hatib et al. |
| 2010/0099964 | A1 | 4/2010 | O'Reilly et al. |
| 2010/0152592 | A1 | 6/2010 | Hatib et al. |
| 2010/0324827 | A1 | 12/2010 | Addison et al. |
| 2011/0270097 | A1 | 11/2011 | Aboy et al. |
| 2013/0226009 | A1* | 8/2013 | Mestek ............... A61B 5/7275 600/479 |
| 2014/0073889 | A1 | 3/2014 | Su et al. |
| 2014/0073890 | A1 | 3/2014 | Su et al. |
| 2014/0073962 | A1 | 3/2014 | Addison et al. |
| 2014/0316278 | A1 | 10/2014 | Addison et al. |
| 2014/0316287 | A1 | 10/2014 | Watson et al. |
| 2014/0323824 | A1 | 10/2014 | Addison et al. |
| 2014/0323874 | A1 | 10/2014 | Addison et al. |
| 2014/0323876 | A1 | 10/2014 | McGonigle et al. |
| 2015/0359442 | A1 | 12/2015 | Knoll |
| 2016/0015284 | A1 | 1/2016 | Grudic et al. |
| 2016/0073965 | A1 | 3/2016 | Addison et al. |
| 2017/0027502 | A1 | 2/2017 | Nikolic |
| 2017/0202536 | A1 | 7/2017 | Murthi |
| 2017/0273573 | A1 | 9/2017 | Tusman et al. |
| 2017/0332919 | A1 | 11/2017 | Eagle et al. |
| 2017/0332995 | A1 | 11/2017 | Eibl et al. |
| 2017/0360366 | A1 | 12/2017 | Potes et al. |
| 2018/0000360 | A1 | 1/2018 | Addison et al. |
| 2019/0046113 | A1 | 2/2019 | Nikolic |
| 2020/0032336 | A1 | 1/2020 | Sensen et al. |

FOREIGN PATENT DOCUMENTS

| | | |
|---|---|---|
| JP | 2018502612 A | 2/2018 |
| WO | 2012150258 A1 | 11/2012 |

OTHER PUBLICATIONS

Kim et al., "A Novel Particle Filtering Method For Estimation of Pulse Pressure Variation During Spontaneous Breathing", 2016, BioMed Eng Online (Year: 2016).*

A. A. Arikan, M. Zappitelli, S. L. Goldstein, A. Naipaul, L. S. Jefferson, and L. L. Loftis, "Fluid overload is associated with impaired oxygenation and morbidity in critically ill children," Pediatr. Crit. Care Med., 2012, pp. 253-258, vol. 13, No. 3, DOI:10.1097/PCC.0b013e31822882a3.

A. S. Bronzwaer, D. M. Ouweneei, W. J. Stok, B. E. Westerhof, and J. J. Van Lieshout, "Arterial pressure variation as a biomarker of preload dependency in spontaneously breathing subjects—A proof of principle," PLoS One, 2015, 11 pgs., vol. 10, No. 9, DOI: 10.1371/journal.pone.0137364.

A. Szold, R. Pizov, E. Segal, and A. Perel, "The effect of tidal vol. and intravascular vol. state on systolic pressure variation in ventilated dogs.," Intensive Care Med., 1989, pp. 368-371, vol. 15, Springer-Verlag.

A. Y. Denault, J. Gorcsan, and M. R. Pinsky, "Dynamic effects of positive-pressure ventilation on canine left ventricular pressure—volume relations.," J. Appl. Physiol., 2001, pp. 298-308, vol. 91, No. 1, American Physiiological Society.

B. C. Morgan, E. W. Crawford, and W. G. Guntheroth, "The Hemodynamic Effects of Changes in Blood Volume during Intermittent Positive-Pressure Ventilation," Anesthesiology, Mar. 1969, pp. 297-305, vol. 30, No. 3.

B. C. Morgan, W. E. Martin, T. F. Hornbein, E. W. Crawford, and W. G. Guntheroth, "Hemodynamic effects of intermittent positive pressure respiration," Anesthesiology, 1966, pp. 584-590, vol. 27, No. 5.

B. Lansdorp et al., "Mechanical ventilation-induced intrathoracic pressure distribution and heart-lung interactions," Crit. Care Med., Sep. 2014, pp. 1983-1990, vol. 42, No. 9, DOI: 10.1097/CCM. 0000000000000345.

D. A. Reuter et al., "Influence of tidal volume on left ventricular stroke vol. variation measured by pulse contour analysis in mechanically ventilated patients," Intensive Care Med., Feb. 11, 2003, pp. 476-480, vol. 29, No. 3, DOI: 10.1007/S00134-003-1649-7.

D. De Backer and M. R. Pinsky, "Can one predict fluid responsiveness in spontaneously breathing patients?," Intensive Care Med., May 17, 2007, pp. 1111-1113, vol. 33, No. 7, PMID: 17508200.

D. De Backer, F. S. Taccone, R. Holsten, F. Ibrahimi, and J. L. Vincent, "Influence of respiratory rate on stroke volume variation in mechanically ventilated patients," Anesthesiology, May 2009, pp. 1092-1097, vol. 110, No. 5, DOI: 10.1097/ALN.0b013e31819db2a1.

D. De Backer, S. Heenan, M. Piagnerelli, M. Koch, and J. L. Vincent, "Pulse pressure variations to predict fluid responsiveness: Influence of tidal volume," Intensive Care Med., Mar. 8, 2005, pp. 517-523, vol. 31, No. 4, DOI: 10.1007/00134-005-2586-4.

D. Han et al., "Different predictivity of fluid responsiveness by pulse pressure variation in children after surgical repair of ventricular septal defect or tetralogy of Fallot," Paediatr. Anaesth., 2017, pp. 1056-1063, vol. 27, No. 10, DOI: 10.1111/pan.13218.

D. M. Hong, J. M. Lee, J. H. Seo, J. J. Min, Y. Jeon, and J. H. Bahk, "Pulse pressure variation to predict fluid responsiveness in spontaneously breathing patients: Tidal vs forced inspiratory breathing," Anaesthesia, 2014, pp. 717-722, vol. 69, No. 7, DOI: 10.1111/anae. 12678.

David Andrew Pybus, "Real-time, spectral analysis of the arterial pressure waveform using a wirelessly-connected, tablet computer: a pilot study," Apr. 28, 2018, Journal of Clinical Monitoring and Computing, pp. 53-63, vol. 33, Springer.

É. Zöllei et al., "Non-invasive detection of hypovolemia or fluid responsiveness in spontaneously breathing subjects," BMC Anesthesiol., 2013, 8 pgs., vol. 13:40, DOI: 10.1186/1471-2253-13-40.

F. Jardin, J.-C. Farcot, P. Gueret, J.-F. Prost, Y. Ozier, and J.-P. Boudarias, "Cyclic changes in arterial pulse during respiratory support," Circulation, Aug. 1983, pp. 266-274, vol. 68, No. 2.

F. Michard and J.-L. Teboul, "Predicting Fluid Responsiveness in ICU Patients. A Critical Analysis of the Evidence," Chest, Jun. 2002, pp. 2000-2008, vol. 121, DOI: 10.1378/chest.121.6.2000.

F. Michard and J.-L. Teboul, "Using heart-lung interactions to assess fluid responsiveness during mechanical ventilation," Crit. Care, Sep. 1, 2000, pp. 282-289, vol. 4.

F. Michard, "Changes in Arterial Pressure during Mechanical Ventilation," Anesthesiology, Aug. 2005, pp. 419-128, vol. 103.

F. Michard, et al., "Relation between Respiratory Changes in Arterial Pulse Pressure and Fluid Responsiveness in Septic Patients with Acute Circulatory Failure," Am. J. Respir. Crit. Care Med., 2000, pp. 134-138, vol. 162, DOI: 10.1164/ajrccm.162.1.9903035.

F. Piccioni, F. Bernasconi, G. T. A. Tramontano, and M. Langer, "A systematic review of pulse pressure variation and stroke volume variation to predict fluid responsiveness during cardiac and thoracic surgery," J. Clin. Monit. Comput., Jun. 15, 2016, pp. 677-684, vol. 31, No. 4, DOI: 10.1007/s10877-016-9898-5.

H. Gan, M. Cannesson, J. R. Chandler, and J. M. Ansermino, "Predicting fluid responsiveness in children: A systematic review," Anesth. Analg., Dec. 2013, pp. 1380-1392, 2013, vol. 117, No. 6, DOI: 10.1213/ANE.0b013e3182a9557e.

H. Theres et al., "Phase-related changes in right ventricular cardiac output under vol. controlled mechanical ventilation with positive end-expiratory pressure," Crit. Care Med., May 1999, pp. 953-958, vol. 27, No. 5, DOI: 10.1097/00003246-199905000-00033.

ISA/EPO, "International Search Report and Written Opinion," dated Jun. 2, 2020, 12 pages.

(56) References Cited

OTHER PUBLICATIONS

J. Mesquida, H. K. Kim, and M. G. Pinsky, "Effect of tidal volume intrathoracic pressure, and cardiac contractility on variations in pulse pressure, stroke volume and intrathoracic blood volume," Intensive Care Med., Jul. 8, 2011, pp. 1672-1679, vol. 37,DOI: 10.1007/s00134-011-2304-3.

J. Renner, et al., "Prediction of fluid responsiveness in infants and neonates undergoing congenital heart surgery," Br. J. Anaesth., Nov. 23, 2011, pp. 108-115, vol. 108, No. 1.

J. Y. Lee, J. Y. Kim, C. H. Choi, H. S. Kim, K. C. Lee, and H. J. Kwak, "The ability of stroke volume variation measured by a noninvasive cardiac output monitor to predict fluid responsiveness in mechanically ventilated children," Pediatr. Cardiol., 2014, pp. 289-294, vol. 35, No. 2, DOI: 10.1007/s00246-013-0772-7, Springer.

M. Canesson, M. Aboy, C. K. Hofer, and M. Rehman, "Pulse pressure variation: Where are we today?," J. Clin. Monit. Comput., 2011, pp. 45-56, vol. 25, No. 1, DOI: 10.1007/s10877-010-9229-1.

N. Do and L. Kunyansky, "Theoretically exact photoacoustic reconstruction from spatially and temporally reduced data," Jun. 25, 2018, PMCID: http://arxiv.org/abs/1806.08412.

NPL—International Search Report, Jun. 2, 2020, 12 pages.

P. E. Marik, and J. Lemson, "Fluid responsiveness: An evolution of our understanding," Br. J. Anaesth, Feb. 16, 2014, pp. 617-620, vol. 112, No. 4, DOI: 10.1093/bja/aet590.

P. E. Marik, R. Cavallazzi, T. Vasu, and A. Hirani, "Dynamic changes in arterial waveform derived variables and fluid responsiveness in mechanically ventilated patients: A systematic review of the literature," Crit. Care Med., 2009, pp. 2642-2647, vol. 37, No. 9, DOI: 10.1097/CCM.0b013e3181a590da.

R. C. de F. Chaves et al., "Assessment of fluid responsiveness in spontaneously breathing patients: a systematic review of literature," Ann. Intensive Care, Dec. 2018, 10 pgs., vol. 8, No. 1, DOI: 10.1186/s13613-018-0365-y.

Robert H Thiele et al., Radial-femoral concordance in time and frequency domain-based estimates of systemic arterial respiratory variation, Aug. 19, 2012, J. Clin. Monit. Comput., pp. 393-400, vol. 26, Springer Science+Business Media, LLC.

S. Heenan, D. De Backer, and J. L. Vincent, "How can the response to vol. expansion in patients with spontaneous respiratory movements be predicted?," Crit. Care, 2006, 7 pgs., vol. 10, No. 4, DOI: 10.1186/cc4970.

S. N. Myatra, N. R. Prabu, J. V. Divatia, X. Monnet, A. P. Kulkarni, and J. L. Teboul, "The Changes in Pulse Pressure Variation or Stroke Volume Variation after a 'tidal Volume Challenge' Reliably Predict Fluid Responsiveness during Low Tidal Volume Ventilation," Crit. Care Med., Mar. 2017, pp. 415-421, vol. 45, No. 3, DOI: 10.1097/CCM.0000000000002183.

S. Scharf, R. Brown, N. Saunders, and L. Green, "Hemodynamic effects of positive-pressure inflation," J. Appl. Physiol Resp. Environ. Exerc. Physiol., 1980, pp. 124-131, vol. 49, No. 1.

S. Soubrier, et al., "Can dynamic indicators help the prediction of fluid responsiveness in spontaneously breathing critically ill patients?," Intensive Care Med., 2007, pp. 1117-1124, vol. 33, No. 7, DOI: 10.1007/s00134-007-0644-9.

Won Jung Shin et al., "Spectral analysis of respiratory-related hemodynamic variables in simulated hypovolemia: a study in healthy volunteers with spontaneous breathing using a paced breathing activity," Jun. 2010, pp. 542-549, vol. 58(6), Korean J. Anesthesiol.

X. Monnet, P. E. Marik, and J. L. Teboul, "Prediction of fluid responsiveness: An update," Ann. Intensive Care, Dec. 2016, 11 pgs., vol. 6, No. 1, ,DOI: 10.1186/s13613-016-0216-7.

Nobutaka Ono, Fundamentals and applications of short-time Fourier transform, The Journal of the Acoustical Society of Japan, 2016, vol. 72, Issue 12, pp. 764-769, Released on J-STAGE Jun. 1, 2017, Online ISSN 2432-2040, Print ISSN 0369-4232, https://doi.org/10.20697/jasj.72.12_764, https://www.jstage.jst.go.jp/article/jasj/72/12/72_764/_article/-char/en.

\* cited by examiner

METHOD OF PREDICTING FLUID RESPONSIVENESS IN PATIENTS

TECHNICAL FIELD

The present invention relates to the field of medicine, and in particular to techniques for predicting fluid responsiveness in critically ill patients.

BACKGROUND ART

Critically ill patients are vulnerable to organ injury/failure due to cellular hypoxia and thus preservation of adequate oxygen delivery is at the core of critical care medicine. Fluid resuscitation is routinely employed in states of shock when augmentation of preload is presumed to lead to improvement in cardiac output. Fluid responsiveness defines a state where administration of fluid resuscitation leads to an increase in cardiac output, i.e. residing on the ascending segment of the Frank-Starling curve. Improvement of blood flow leads to reduction tissue hypoxia, but alternatively fluid administration without raised cardiac output can lead to further organ injury and morbidity. In studies designed to examine fluid responsiveness, only 40-70% of adults with circulatory failure demonstrated an increase in cardiac output with fluid administration.

SUMMARY OF INVENTION

According to one aspect, a method of predicting fluid responsiveness in a critically ill patient comprises: measuring a real-time physiological data of the patient, producing a real-time physiological waveform; performing a discrete Fourier transform of the real-time physiological waveform; generating an estimate of pulse pressure variability from the discrete Fourier transform of the real-time physiological waveform; and displaying the estimate of pulse pressure variability on a clinical display.

According to a second aspect, a non-transitory machine-readable medium stores instructions for predicting fluid responsiveness in a critically ill patient, comprising instructions that when executed cause a programmable device to: measure a real-time physiological data of the patient, producing a real-time physiological waveform; perform a discrete Fourier transform of the real-time physiological waveform; generate an estimate of pulse pressure variability from the discrete Fourier transform of the real-time physiological waveform; and display the estimate of pulse pressure variability on a clinical display.

According to a third aspect, a physiological monitoring system comprises: a programmable device; a storage medium on which are stored instructions for predicting fluid responsiveness in a critically ill patient, comprising instructions that when executed cause the programmable device to: measure a real-time physiological data of the patient, producing a real-time physiological waveform; perform a discrete Fourier transform of the real-time physiological waveform; generate an estimate of pulse pressure variability from the discrete Fourier transform of the real-time physiological waveform; and display the estimate of pulse pressure variability on a clinical display.

BRIEF DESCRIPTION OF DRAWINGS

The accompanying drawings, which are incorporated in and constitute a part of this specification, illustrate an implementation of apparatus and methods consistent with the present invention and, together with the detailed description, serve to explain advantages and principles consistent with the invention. In the drawings.

DESCRIPTION OF EMBODIMENTS

Figure 1:
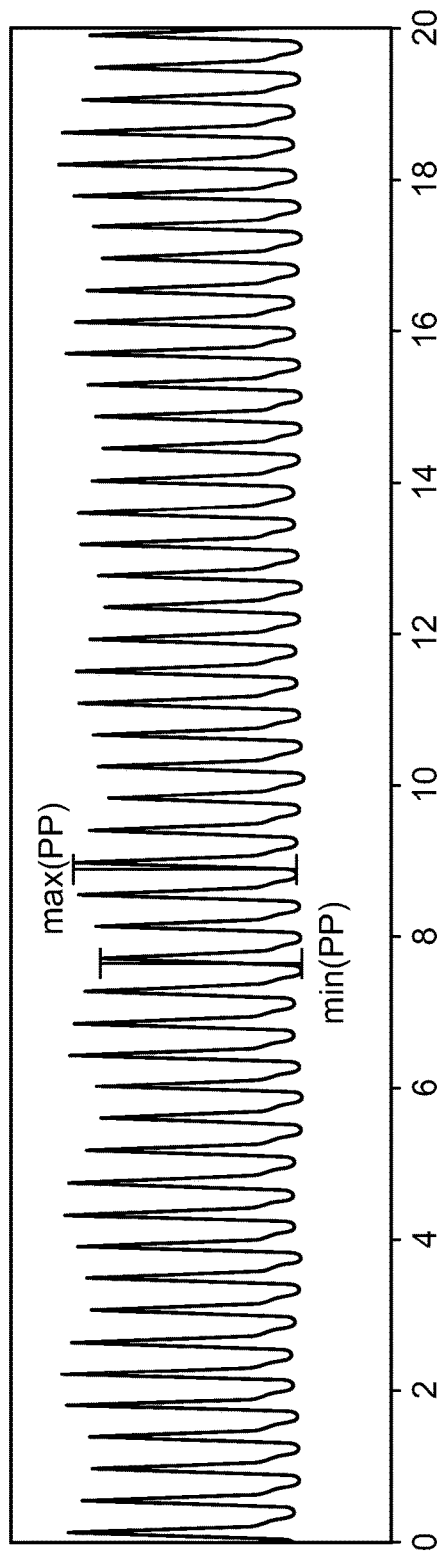
FIG. 1 is a graph of an arterial blood pressure waveform.

In the following description, for purposes of explanation, numerous specific details are set forth in order to provide a thorough understanding of the invention. It will be apparent, however, to one skilled in the art that the invention may be practiced without these specific details. In other instances, structure and devices are shown in block diagram form in order to avoid obscuring the invention. References to numbers without subscripts are understood to reference all instance of subscripts corresponding to the referenced number. Moreover, the language used in this disclosure has been principally selected for readability and instructional purposes, and may not have been selected to delineate or circumscribe the inventive subject matter, resort to the claims being necessary to determine such inventive subject matter. Reference in the specification to "one embodiment" or to "an embodiment" means that a particular feature, structure, or characteristic described in connection with the embodiments is included in at least one embodiment of the invention, and multiple references to "one embodiment" or "an embodiment" should not be understood as necessarily all referring to the same embodiment.

A clinician's ability to gauge intravascular volume status based on bedside exam (skin turgor, urine output) and commonly measured static variables such as heart rate, central venous pressure, pulmonary artery occlusion pressure, or blood pressure have consistently shown to be poor. Pulse pressure variation (PPV), systolic pressure variation (SPV), and stroke volume variation (SVV) are dynamic variables derived from cardiorespiratory interactions and are well established in predicting fluid responsiveness.

Blood pressure variation during cyclic respiratory phases has been demonstrated to be a useful marker for signaling hypovolemia. The physiologic mechanism for the magnitude of PPV has been linked to intravascular volume status. With positive pressure ventilation, Morgan et al. showed a reduction in vena cava blood flow during the early inspiratory phase, followed by a reduction in pulmonary blood flow, and lastly a reduction in aortic blood flow two cardiac cycles later. They subsequently showed a decline in cardiac output (CO) with increasing mean airway pressures, and improvement in CO after fluid administration. Denault et al. have shown that an additional impact of positive pressure ventilation is the effect on the reduction of left atrial transmural pressure leading to reduced left ventricular preload.

At a given arterial compliance, pulse pressure amplitude and variation are directly related to left ventricular (LV) stroke volume. The initial increase in stroke volume with the positive pressure inspiratory phase is due to an increase in trans-pulmonary pressure (alveolar pressure minus pleural pressure) causing a "squeezing effect" of the pulmonary capillaries leading to increased left atrial return and a reduction in left ventricular afterload due to reduced LV transmural pressure. The delayed (pulmonary transit interval) decrease in LV stroke is a result of reduced right atrial venous return and increased right ventricle (RV) afterload. The reduced RV stroke volume is more pronounced in patients with hypovolemia due to: 1) collapse of central veins due to increased intrathoracic pressure, 2) reduced gradient to venous return from reduced right atrial transmural pressure, 3) higher chance of encountering West zone I and II (pulmonary art pressure<Alveolar pressure, pulmonary venous pressure<Alveolar pressure) conditions in hypovolemic state, with resulting increased RV afterload, 4) a set change in preload leads to a greater change in stroke volume on the ascending (preload dependent) portion of the Frank-Starling curve. Numerous studies have shown that under hypovolemic conditions, the magnitude of arterial pressure variation is greatest in the expiratory phase, as an expected consequence of pulmonary transit.

Multiple studies beginning with Michard et al. in 2000 have defined stroke volume and pulse pressure variation (PPV) thresholds (approximately >14% variation) with positive pressure variation at which patients are fluid responsive. A meta-analysis including 22 studies with 800 patients has found a pooled sensitivity of 88% and specificity of 89%, when utilizing a pulse pressure variation of 13% in predicting fluid responsiveness. There are only a few studies in the pediatric population. A meta-analysis of 12 studies and 438 patients found dynamic variables, including pulse pressure variation and systolic pressure variation, were not able to predict fluid responsiveness. There are four studies limited to patients with atrial septal defects, ventricular septal defects, and/or tetralogy of Fallot that have found pulse pressure variation or stroke volume variation to predict fluid responsive in the post-operative period.

With spontaneous breathing (SB) or negative pressure ventilation, an inverse effect would be anticipated based on the cardiopulmonary interactions. During inspiration, intrathoracic pressure would decrease and there would be greater venous return to the right heart. This would be followed by a pulmonary transit delay (2-3 cardiac cycles) after which left ventricular preload would be augmented. Thus, during the expiratory phase, if an increase in cardiac output occurred then there would be an increase in the pulse pressure and systolic pressure amplitude. An additional effect would be an increase in the aortic transmural pressure with inspiration, leading to a reduction in the stroke volume. Similar to positive pressure ventilation, the amplitude of pulse pressure change may be impacted by the loading conditions created by the intrathoracic pressure change. Soubrier et al. evaluate 32 adult patients who received volume expansion and found PPV (using a 12% threshold) to have a high specificity (92%) and low sensitivity (63%) in predicting fluid responsiveness. The authors concluded SB to be less reliable than positive pressure ventilation in predicting fluid responsiveness due to low sensitivity.

It should be noted that in both cases, positive and negative pressure ventilation, the effect of cardio-pulmonary interactions is dependent on tidal volume among other parameters. Independent of the intravascular volume status, lower tidal volume will necessarily induce a weaker cardiopulmonary interaction. In that case, cyclic variations in cardiac filling may not be great enough to induce a measurable PPV. The present disclosure is focused on the robust measurability of small PPV. This smallness can be consequence of a lack of fluid responsiveness (plateau of Frank-Starling curve) or low tidal volume ventilation. Our objective is twofold. First, to reveal some shortcomings of the traditional algorithms employed to process arterial blood pressure (ABP) measurements into an estimation of PPV. The second objective is to propose a new algorithm capable of greater precision and robustness, especially in the small PPV regime where noise can easily overwhelm the physiologic signals.

The traditional algorithms to estimate PPV are based on finding the systolic peaks and diastolic troughs in the arterial pressure waveform. Consequently, the pulse pressure (PP) can be estimated on a beat-by-beat basis. Then, within a respiratory cycle, the maximum PP and minimum PP are found, which plugged into the following definition of PPV:

$$PPV_{old} = 2\frac{\max(PP) - \min(PP)}{\max(PP) + \min(PP)} \quad (1)$$

Thus, an estimation of PPV is obtained at every respiratory cycle or an average of such estimations can be computed over many respiratory cycles in order to reduce the effect of noise. An illustration of the maximum PP and minimum PP within a respiratory cycle is shown in FIG. 1, which graphs a patient's arterial blood pressure waveform, where Max(PP) means the maximum pulse pressure over a respiratory cycle, and Min(PP) means the minimum pulse pressure over a respiratory cycle. The traditional technique is based on the detection of peaks and troughs in the waveform to estimate pulse pressure on a beat-by-beat basis and find its maximum and minimum values over each respiratory cycle.

Figure 2:
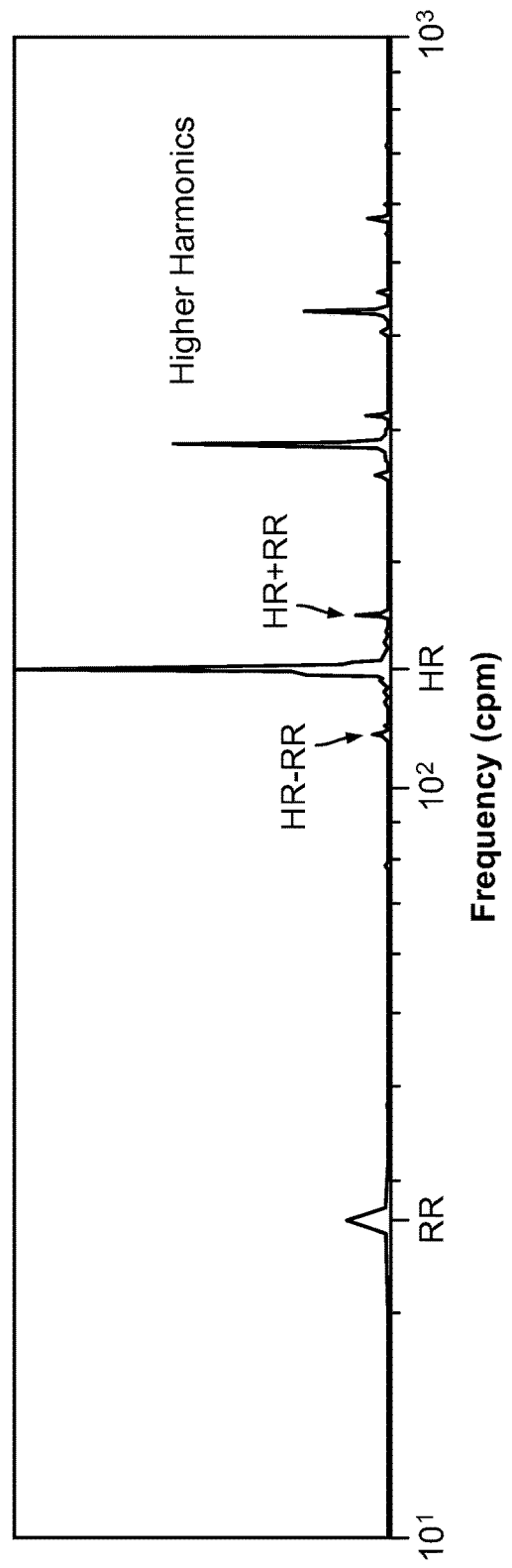
FIG. 2 is a Fourier transform of the waveform of FIG. 1.

In order to motivate the development of the proposed technique, we analyze the Fourier transform shown in FIG. 2 of the arterial blood pressure waveform shown in FIG. 1. The blood pressure waveform contains a cardiac component $u_c(t)$ oscillating at the heart rate (HR). The cyclic changes of the intrathoracic pressure influence the cardiac pumping, inducing a modulation of pulse pressure (amplitude of the cardiac component) which can be expressed as the product $A_r(t)u_c(t)$ where the amplitude modulation $A_r(t)$ oscillates at the respiratory rate (RR). The product of functions in the time domain translates into convolution of factors in the frequency domain. We see these features in FIG. 2. The Fourier transform of this real-valued signal is also supported on the negative side of the frequency axis. The value of the Fourier transform at a negative frequency is the complex conjugate of its value at the corresponding positive frequency. In FIG. 2, we note the presence of peaks at the respiratory rate (RR) and at the heart rate (HR). There are complex-conjugate peaks at the frequencies (−RR) and (−HR). The cardiac peak at the (HR), is convolved with the respiratory peaks at (RR) and (−RR), giving raise to energy supported in the vicinity of (HR−RR) and (HR+RR), respectively. In other words, the influence of the oscillatory intrathoracic pressure on the circulatory system induces the appearance of peaks at the frequencies (HR−RR) and (HR+RR) as seen in FIG. 2. The new technique proposed herein is based on this observation and on the detection of convolved Fourier components in the vicinity of the frequencies (HR−RR) and (HR+RR).

FIG. 2 illustrates a patient's arterial blood pressure waveform and the absolute value of its Fourier transform, where RR means Respiratory rate and HR means Heart rate. The proposed technique to measure PPV is based on the detection of the convolved components supported in the vicinity of the frequencies HR−RR and HR+RR as described by the mathematical analysis of the cardiopulmonary interaction.

The technique proposed in this disclosure is based on the frequency analysis, using the Fourier transform, of the arterial blood pressure waveform. It is assumed that this signal can be modeled as follows:

$$u(t) = u_m + (1 + \alpha u_r(t+t_d))u_c(t) + u_r(t) + \eta(t), \quad (2)$$

where $u_m$ is the mean value of $u(t)$, $u_r(t)$ is the respiratory component, $u_c(t)$ is the cardiac component, and $\eta(t)$ represents random noise. The factor $(1+\alpha u_r(t+t_d))$ represents the time-modulation of the cardiac oscillations (pulse pressure) which oscillates at the frequency of the respiratory component $u_r$. The factor $\alpha \leq 0$, known as the transmission coefficient, quantifies the portion of the respiratory component that affects the pulse pressure modulation. We allow for the presence of a time delay $t_d$ between the respiratory component $u_r(t)$ and the time-modulation of cardiac amplitude $(1+\alpha u_r(t+t_d))$. The respiratory pressure oscillations induce fluctuations in the loading conditions of the right and left ventricles. The fluctuations in right ventricle loads lead to oscillations in left ventricle filling after a phase lag due to the blood flow pulmonary transit time. This lag is accounted for by the time delay $t_d \leq 0$.

Under the assumed form (2), the pulse pressure variability (PPV) is given by:

$$PPV = 2\frac{\max_t(1+\alpha\, u_r(t+t_d)) - \min_t(1+\alpha\, u_r(t+t_d))}{\max_t(1+\alpha\, u_r(t+t_d)) + \min_t(1+\alpha\, u_r(t+t_d))} = \frac{2\alpha\,(\max(u_r)-\min(u_r))}{2+\alpha(\max(u_r)+\min(u_r))}.$$

Assuming that the respiratory component $u_r$ oscillates with equal magnitude above and below zero, that is, $\min(u_r) = -\max(u_r)$ then the formula for PPV simplifies to:

$$PPV = 2\alpha\,\max(u_r). \quad (3)$$

In order to make practical use of this formula, it is needed to estimate the transmission coefficient $\alpha$ and the amplitude of the respiratory component $\max(u_r)$ from the measured signal $u(t)$. We accomplish this task using the Discrete Fast Fourier Transform $\mathcal{F}$ with discrete frequencies ranging from $-f_s/2$ to $+f_s/2$ where $f_s$ is the frequency at which the signal $u(t)$ is sampled. In the frequency domain, the respiratory component $\mathcal{F}(u_r)$ has a spectral support away from other components. Therefore, it can be isolated from the rest of the signal. The amplitude can be estimated as follows:

$$\max(u_r) \approx \sqrt{2}\|\mathcal{F}(u_r)\|. \quad (4)$$

The discrete $l^2$ norm $\|\cdot\|$ and the discrete Fourier transform $\mathcal{F}$ are normalized by $\sqrt{N}$ where N is the size of the time series signal u.

In order to estimate the transmission coefficient $\alpha$, we use the Fourier-Convolution and the Time-Shift theorems in the model (2) to obtain $$\mathcal{F}(u) = \mathcal{F}(u_m) + \mathcal{F}(u_c) + \alpha[e^{i\omega t_d}\mathcal{F}(u_r)]*\mathcal{F}(u_c) + \mathcal{F}(u_r) + \mathcal{F}(\eta). \quad (5)$$

Since the frequency bands of the respiratory $f_r$ and cardiac $f_c$ components are known and do not overlap, we can simultaneously extract $\mathcal{F}(u_r) = \mathcal{F}(u)|_{f_r}$ and $\mathcal{F}(u_c) = \mathcal{F}(u)|_{f_c}$ from the measured signal $\mathcal{F}(u)$, up to the presence of noise $\mathcal{F}(\eta)$. The convolution $e^{i\omega t_d}\mathcal{F}(u_r)*\mathcal{F}(u_c)$ is supported on the convolved frequencies which we denote by $f_c * f_r$. Therefore, we estimate the transmission coefficient $\alpha$ and the time-shift $t_s$ as the optimizers of the following problem, $$(\alpha_{opt}, t_{d,opt}) = \arg\min \|\mathcal{F}(u)|_{f_c*f_r} - \alpha e^{i\omega t_d}\mathcal{F}(u)|_{f_r} * \mathcal{F}(u)|_{f_c}\| \quad (6)$$

As a result, the unknown parameters $\alpha$ and $t_d$ are fitted to the measured data $\mathcal{F}(u)|_{f_c*f_r}$, $\mathcal{F}(u)|_{f_r}$ and $\mathcal{F}(u)|_{f_c}$. This fitting process leads to a robust technique with respect to the presence of uncorrelated noise. The actual minimization process to obtain these parameters can be carried out by several optimization techniques. We have decided to use the "fminsearch" function built in MATLAB. This technique needs initial guesses to approximate the unknown solution. We are using $\alpha = \|\mathcal{F}(u)|_{f_c*f_r}\|/\|\mathcal{F}(u)|_{f_r}*\mathcal{F}(u)|_{f_c}\|$ and $t_d = 1$ s as the initial guesses. Once the parameters $\alpha$ and $t_d$ are fitted to the data, then we plug the optimal $\alpha_{opt}$ and (4) into (3) to obtain the proposed estimation of the pulse pressure variability $$PPV_{new} = 2\sqrt{2}\alpha_{opt}\|\mathcal{F}(u)|_{f_r}\|. \quad (7)$$

Results

In this section we compare the results from the proposed Fourier-based algorithm to estimate PPV and the traditional algorithm based on peak finding on the signal $u(t)$ in order to find systolic and diastolic points, and estimate the maximum and minimum pulse pressure over each respiratory cycle.

Synthetic Data

Figure 3B:
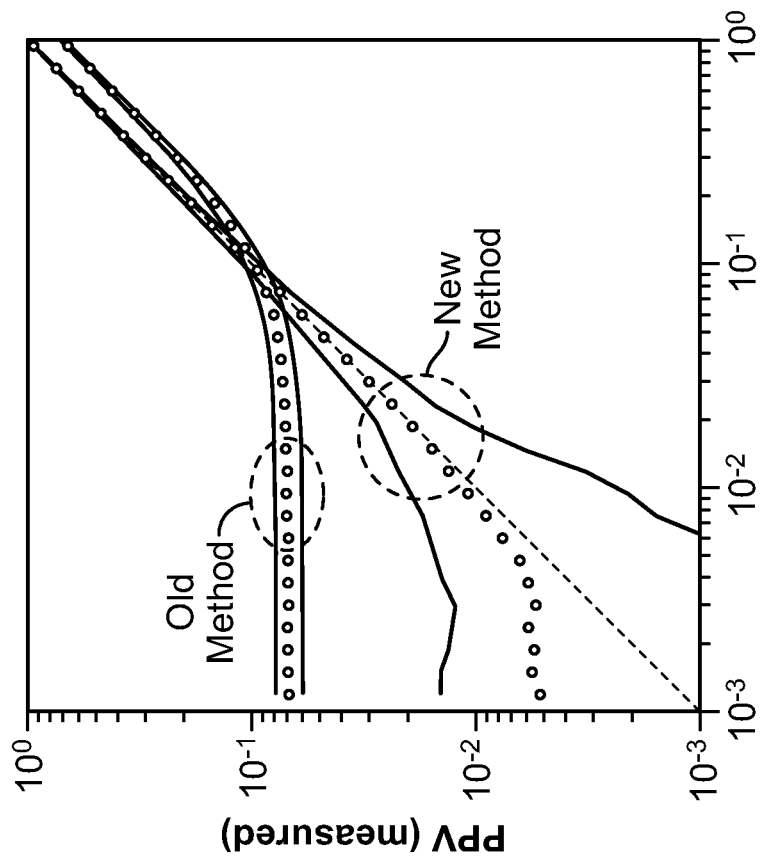
FIGS. 3A-B are graphs comparing a traditional technique for estimating pulse pressure variation (PPV) and a proposed technique according to one embodiment.
Figure 3A:
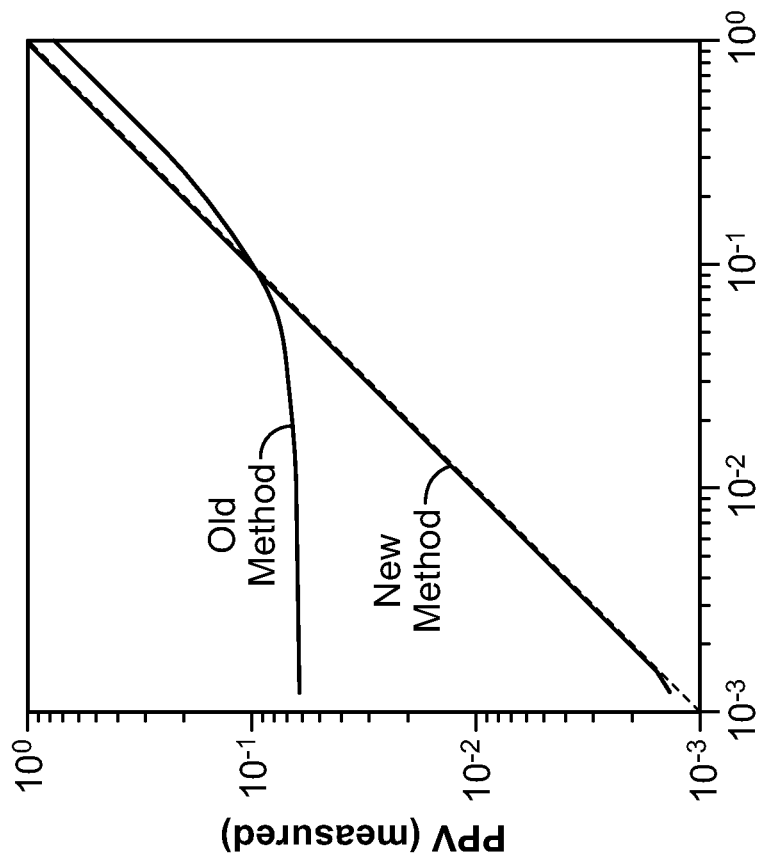

Now we introduce a simple example for the oscillatory signal (2). This synthetic data will allow us to analyze the behavior of the traditional (old) algorithm and of the proposed (new) algorithm. Let $u_m = A_m$, $u_c(t) = A_c \sin(2\pi f_c t)$, $u_r(t) = A_r \sin(2\pi f_r t)$, and let $\eta(t)$ be pink noise. We choose the amplitudes and frequencies as follows: $A_m = 100$ mmHg, $A_c = 20$ mmHg, $A_r = 6$ mmHg, $f_c = 100$ cycles/min, $f_r = 20$ cycles/min. The pink noise is defined so that the standard deviation of $\eta$ is a chosen percentage of the cardiac amplitude $A_c$. The transmission coefficient $\alpha$ is allowed to vary from $10^{-4}$/mmHg to $10^{-1}$/mmHg. FIGS. 3A, B display the behavior of the new and old techniques to estimate the PPV for this test data with 0% and 5% noise, respectively. We realize that, even in the absence of noise, the old technique fails to estimate PPV accurately for small values of PPV. This drawback can be explained mathematically. Even when $\alpha=0$, the presence of $u_r(t)$ in (2) affects the estimation of the peaks and troughs of the cardiac oscillations in $u_c(t)$. In the best-case scenario, when the largest slope of $u_r(t)$ coincides with a peak or trough of $u_c(t)$, then we have that $$\max(PP) = 2A_c + |u_r(t+dt) - u_r(t)| \approx 2A_c + 2\pi f_r A_r dt \cos 2\pi f_r$$

$$\min(PP) = 2A_c - |u_r(t+dt) - u_r(t)| \approx 2A_c + 2\pi f_r A_r dt \cos 2\pi f_r$$

where $dt = 1/(2f_c)$ is half of a cardiac period. Plugging these estimations into (1), we find that the old technique estimates PPV in the limit of small transmission coefficient as follows, $$\lim_{\alpha \to 0} PPV_{old} \geq \pi \frac{A_r f_r}{A_c f_c} \cos\left(\pi \frac{f_r}{f_c}\right). \qquad (8)$$

The actual PPV vanishes when the transmission coefficient goes to zero. However, the old technique overestimates it according to (8) as the measured PPV plateaus as the model PPV approaches zero. This behavior is observed in FIGS. 3A, B with and without the presence of noise in the signal.

FIGS. 3A, B illustrated a comparison between the proposed (new) technique (FIG. 3B) and the traditional (old) technique (FIG. 3A) for estimating PPV. The range of PPV was realized in the model (2) by varying the transmission coefficient $\alpha$ from $10^{-4}$/mmHg to $10^{-1}$/mmHg. In the absence of noise (A), the old technique fails to estimate the PPV accurately for small values of PPV. The new technique is extremely precise for small and large values of PPV. In the presence of 5% pink noise (B), the average of 250 realizations is shown (circles) along with the 5$^{th}$ and 95$^{th}$ percentile curves (solid lines). All of the other parameters are fixed as follows: $A_m$=100 mmHg, $A_c$=20 mmHg, $A_r$=6 mmHg, $f_c$=100 cpm, $f_r$=20 cpm.

Using the new technique, the measured PPV is able to follow the model PPV for an extended range into smaller values of PPV. Even in the presence of 5% noise, the average estimation of the new technique follows the correct behavior down to values of PPV below 0.01. Notice that the size of the noise remains constant for all values of PPV. Therefore, the signal-to-noise ratio decreases as the PPV decreases. That is why the error bounds for the new technique shown in FIG. 3B seem to increase, in the loglog scale, as the PPV decreases. However, these error bounds actually remain relatively constant when plotted in the linear scale.

Figure 4B:
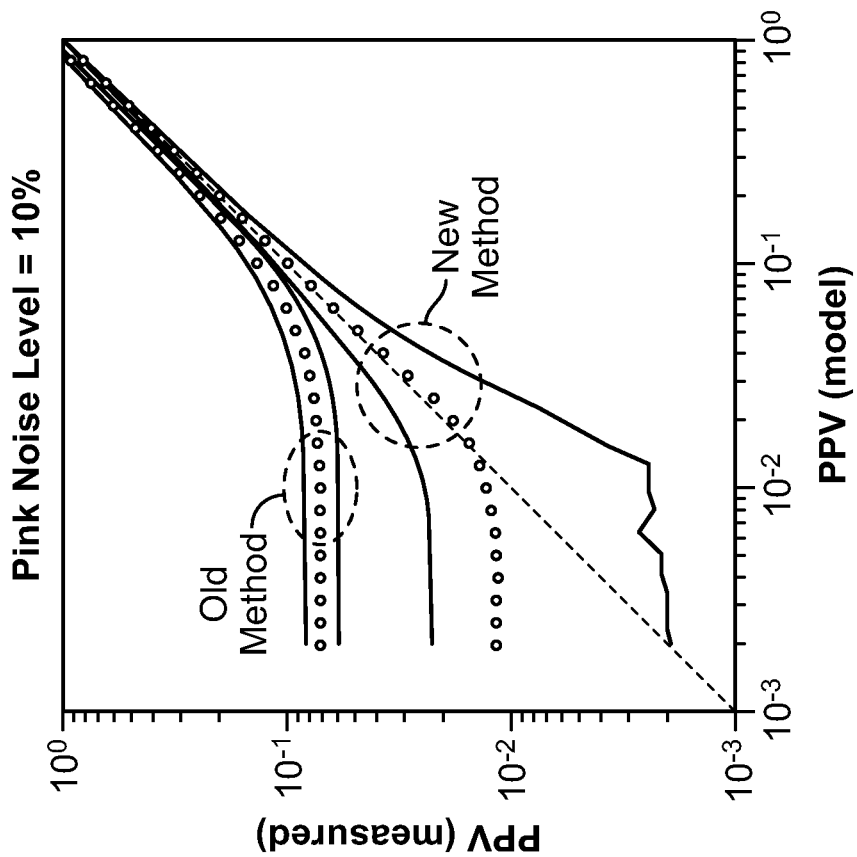
FIGS. 4A-C are graphs comparing a traditional technique for estimating PPV and a proposed technique according to one embodiment in the presence of various amounts of noise.
Figure 4A:
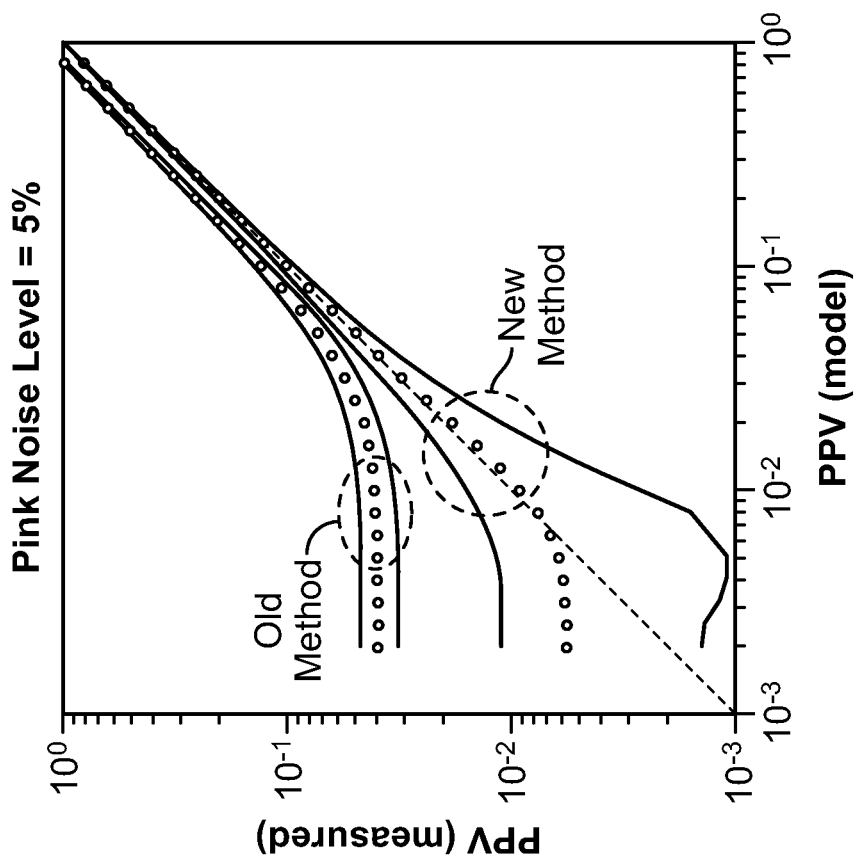
Figure 4C:
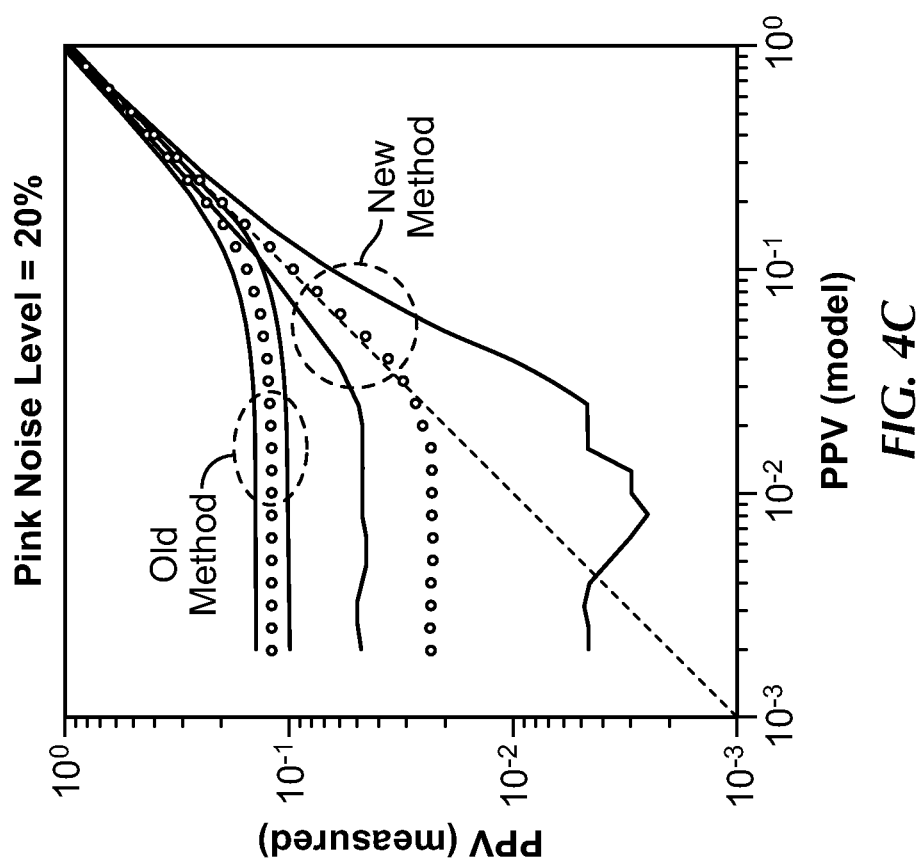

It is known that when breathing is too shallow (low tidal volume), the cardiopulmonary interaction is too small to be measured properly using the traditional technique. The synthetic model allows us to analyze the behavior of both techniques for a range of respiratory amplitudes. We synthetically model this scenario using (2) and letting $u_m = A_m$, $u_c(t) = A_c \sin(2\pi f_c t)$, $u_r(t) = A_r \sin(2\pi f_r t)$, and $\eta(t)$ be pink noise. We choose the amplitudes and frequencies as follows: $A_m$=100 mmHg, $A_c$=20 mmHg, $\alpha$=0.01/mmHg, $f_c$=100 cycles/min, $f_r$=20 cycles/min. The respiratory amplitude $A_r$ is allowed to vary from 0.1 mmHg to 40 mmHg. FIGS. 4A-C display the behavior of the new and old techniques to estimate the PPV for this test data with 5%, 10% and 20% noise. The new technique is much more precise and less sensitive to noise than the old technique. In the average, the new technique follows the correct trend for an extended range of values of PPV, reaching accurate results at values of PPV approximately 6 times smaller than the old technique.

Another way to compare the robustness of these techniques is to estimate the signal-to-noise ratio at which each technique begins to lose accuracy considerably. The amplitude of the sought-after signal is $\alpha A_r A_c$ and the amplitude of noise is given so that $std(\eta) = \sigma A_c$ where $\sigma \geq 0$ is a chosen constant. In FIGS. 4A-C, this constant $\sigma$ is 0.5, 0.1, and 0.2 in each of the respective plots. The signal-to-noise ratio is defined as, $$SNR = \frac{\alpha A_r A_c}{\sigma A_c} = \frac{\alpha A_r}{\sigma}$$

Based on the plots displayed in FIGS. 4A-C, the signal-to-noise ratio at which the old technique begins to lose accuracy is approximately 1:3. On the other hand, for the new technique, this ratio is approximately 1:18.

FIGS. 4A-C illustrate a comparison between the proposed (new) technique and the traditional (old) technique for estimating PPV. The range of PPV was realized in the model (2) by varying the amplitude A_r of the respiratory component from 0.1 mmHg to 40 mmHg. The old technique becomes inaccurate and sensitive to noise when the respiratory amplitude is small. The panels (A), (B) and (C) display results for 5%, 10% and 20% noise, respectively. The average of 250 realizations is shown (circles) along with the 5th and 95th percentile curves (solid lines). In the average, the new technique reaches accurate results at values of PPV approximately 6 times smaller than the old technique. All of the other parameters are fixed as follows: A_m=100 mmHg, A_c=20 mmHg, $\alpha$=0.01/mmHg, f_c=100 cpm, f_r=20 cpm.

Figures 5A, 5B:
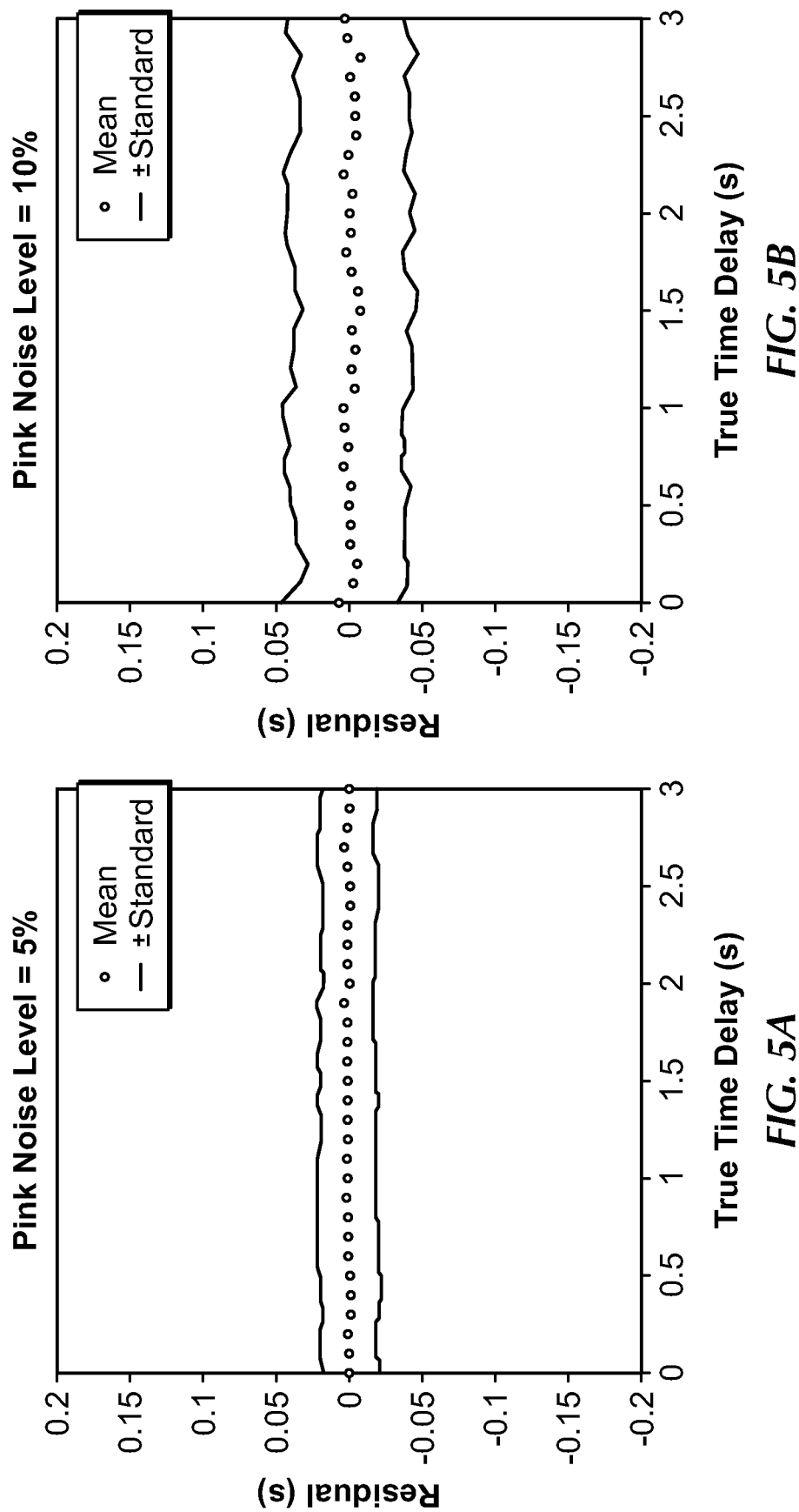
FIGS. 5A-C are graphs illustrating an accuracy of the proposed technique for recovering time delay between mean pressure and pulse pressure oscillations according to one embodiment at various levels of pink noise.
Figure 5C:
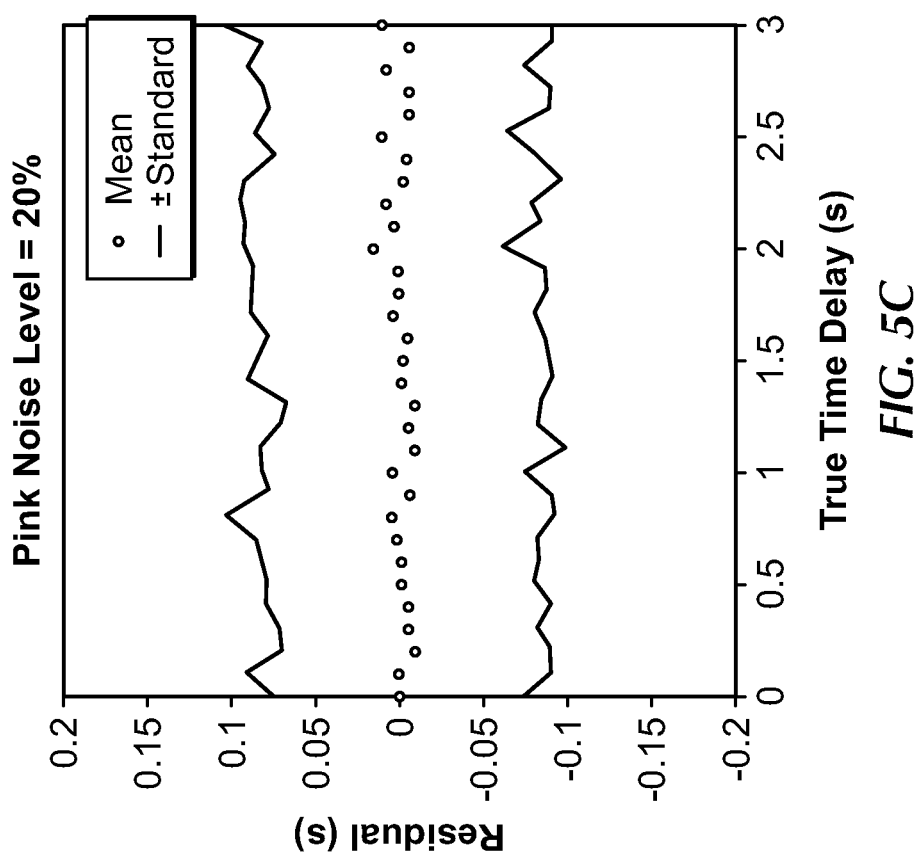

As provided by (6), our new technique is also able to estimate the time delay between the oscillations in mean blood pressure and the oscillations in pulse pressure. The synthetic model allows us to assess the performance of the technique to recover this time delay. We let $u_m = A_m$, $u_c(t) = A_c \sin(2\pi f_c t)$, $u_r(t) = A_r \sin(2\pi f_r t)$, and $\eta(t)$ be pink noise. We choose the amplitudes and frequencies as follows: $A_m$=100 mmHg, $A_c$=20 mmHg, $A_r$=6 mmHg, $\alpha$=0.01/mmHg, $f_c$=100 cpm, $f_r$=20 cpm. FIGS. 5A-C illustrate the performance of the new techniques to estimate the time delay $t_d$ ranging from 0 s to 3 s and for 5%, 10% and 20% pink noise.

FIGS. 5A-C illustrate the accuracy of the new technique to recover the time delay between mean pressure and pulse pressure oscillations. The true value for the time delay $t_d$ was set to range from 0 s to 3 s in the model (2) and pink noise was added to the signal. The panels (A), (B) and (C) display results for 5%, 10% and 20% noise, respectively. For each value of the true time delay, the average of 100 realizations is shown (circles) along with plus/minus one standard deviation (solid lines). All of the other parameters are fixed as follows: $A_m$=100 mmHg, $A_c$=20 mmHg, $A_r$=6 mmHg, $\alpha$=0.01/mmHg, $f_c$=100 cpm, $f_r$=20 cpm.

Real Data

Figure 6:
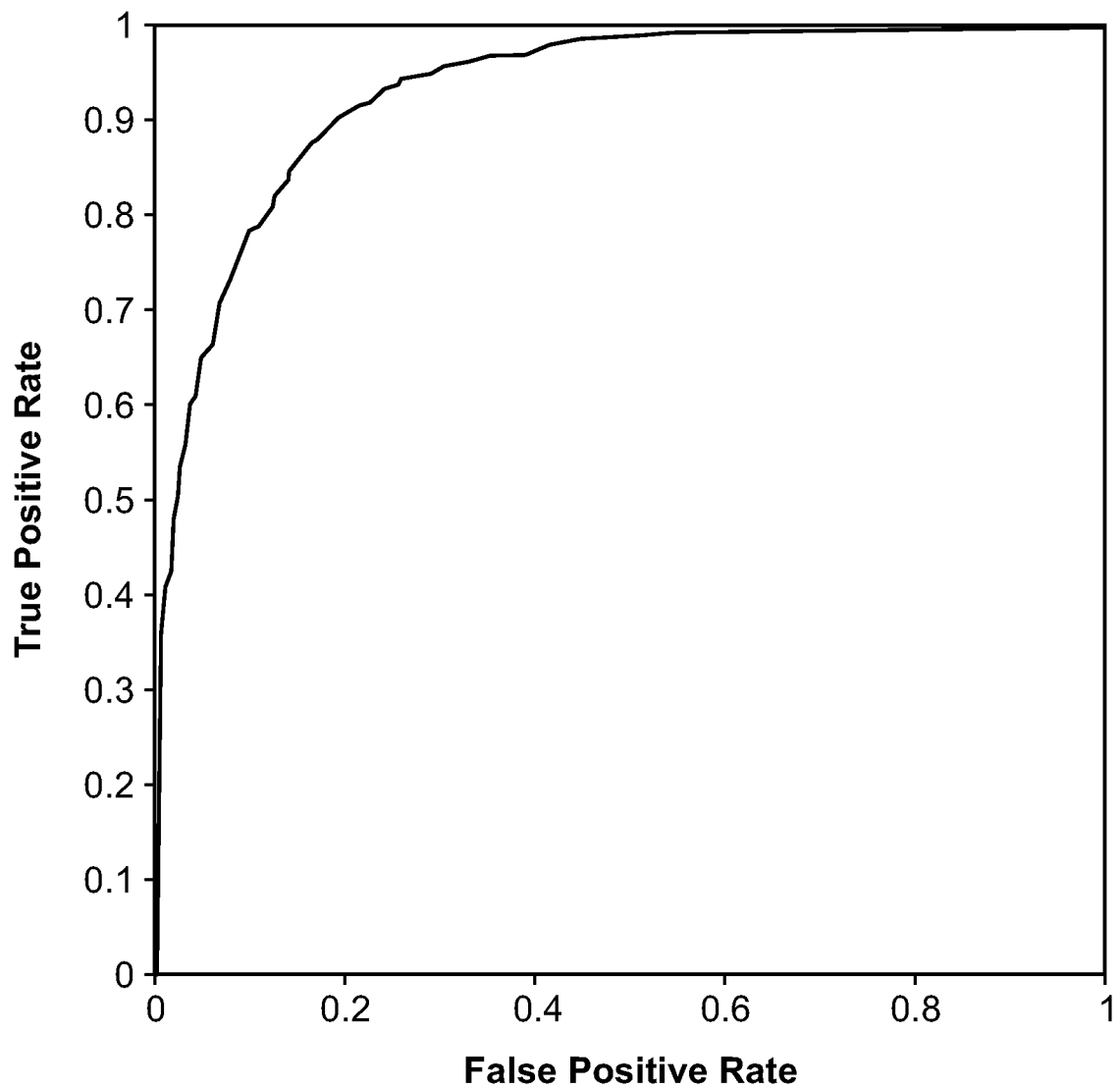
FIG. 6 is a graph illustrating the performance of a logistic regression for discriminating between clean and not clean data according to one embodiment.

In order to properly analyze real data from a large number of patients, a quality measure was developed to filter out inadmissible epochs of data. Six thousand windows (each being one minute long) of blood pressure waveforms were visually inspected and manually labeled as either "clean" or "not clean". Then 6 metrics associated with $\mathcal{F}(u)$ (the Fourier transform of the signal) were defined as factors for a logistic regression to fit the labeling. These metrics are: the spectral power in the cardiac frequency band, the range of the cardiac frequency band, the first and second moments of $|\mathcal{F}(u)|$, the entropy of low frequency components of $|\mathcal{F}(u)|$, and the entropy of the high frequency components of $|\mathcal{F}(u)|$. Half of the data (randomly selected) was employed as a training set to fit the regression coefficients. The other half of the data was employed as a test set to quantify the performance of the logistic regression to discriminate between clean and not clean data. The results are shown in FIG. 6. The area under the ROC curve is 0.94.

FIG. 6 illustrates the performance of the logistic regression to discriminate between clean and not clean data. The area under the ROC curve is 0.94.

Figure 7B:
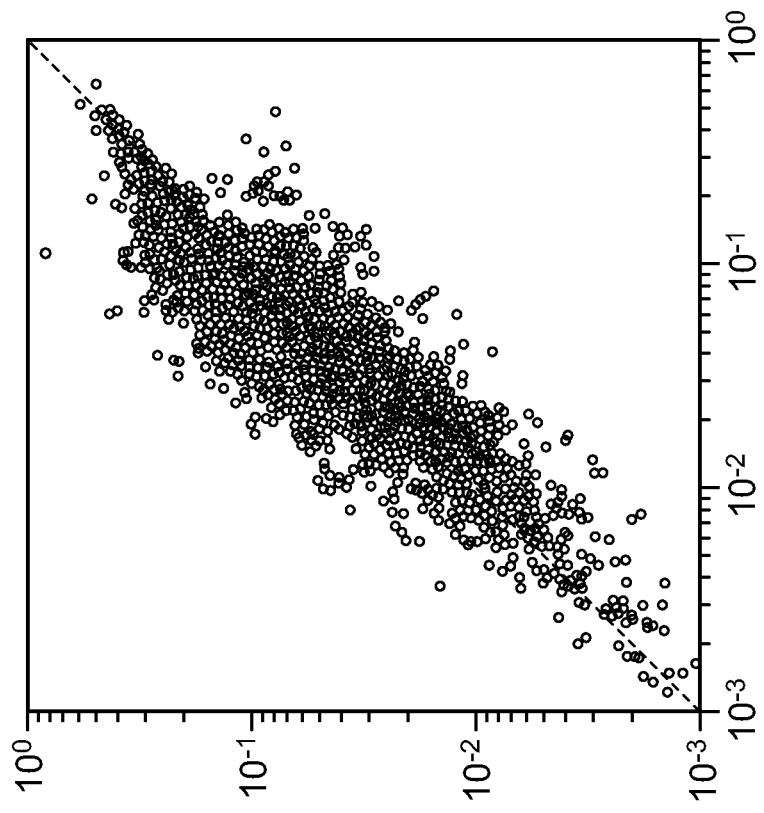
FIGS. 7A-B are graphs illustrating parity plots between a traditional technique for estimating PPV and a proposed technique according to one embodiment.
Figure 7A:
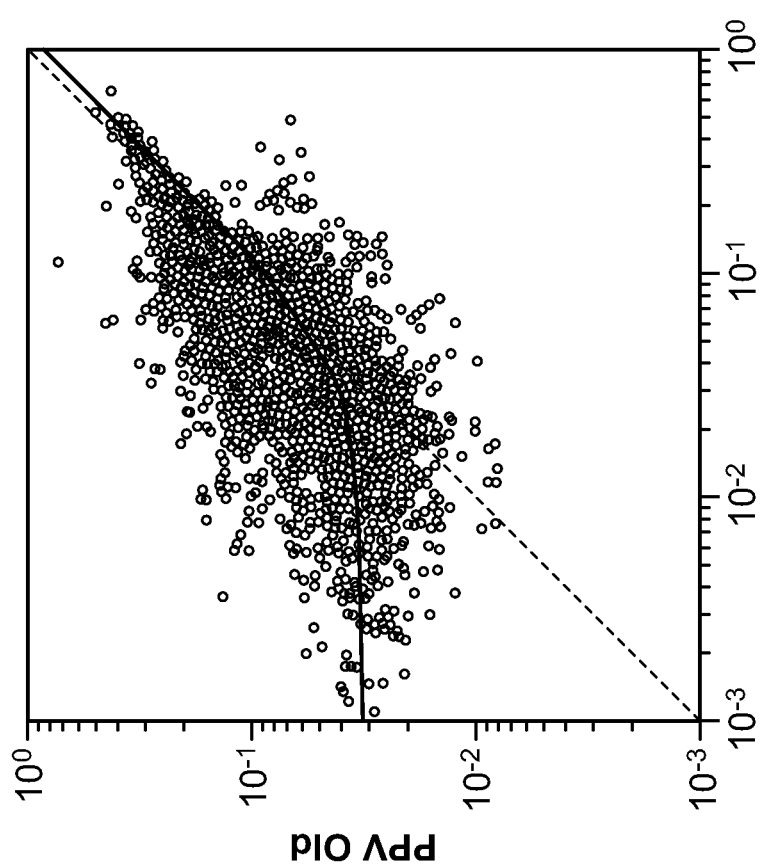

The estimations of PPV from both techniques were compared using parity plots and Pearson's correlation coefficient. A quality threshold equal to 0.15 was chosen to rule out inadmissible data. This threshold renders a true positive rate equal to 98.41% and a false positive rate equal to 46.39%. Approximately 35% of the data is excluded since it falls below this quality threshold. For the admissible data, the parity plots are displayed in FIGS. 7A, B. For the unadjusted old technique, good agreement with the new technique is observed for large values of PPV. However, as expected from the analysis of synthetic data, there is disagreement for small values of PPV due to the old technique's overestimation of PPV in that range. FIG. 7A shows how the real data follows the same behavior observed in the synthetic data. The correlation coefficient is 0.74. FIG. 7B displays the adjusted parity behavior after the model curve from synthetic data was set as the parity line to correct the old technique. This adjusted correlation coefficient is 0.82.

FIGS. 7A, B illustrate parity plots between the proposed (new) technique and the traditional (old) technique for estimating PPV. FIG. 7A shows how the real data follows the same behavior observed in the synthetic data (solid curve). The correlation coefficient is 0.74. FIG. 7B displays the adjusted parity behavior after the synthetic data line (solid curve from left panel) has been set as the parity line to correct the old technique. This adjusted correlation coefficient is 0.82.

The new proposed technique also provides the transmission coefficient $\alpha$ and the time delay $t_d$ for the real data. These results are displayed in FIGS. 8A, B.

Figure 8A:
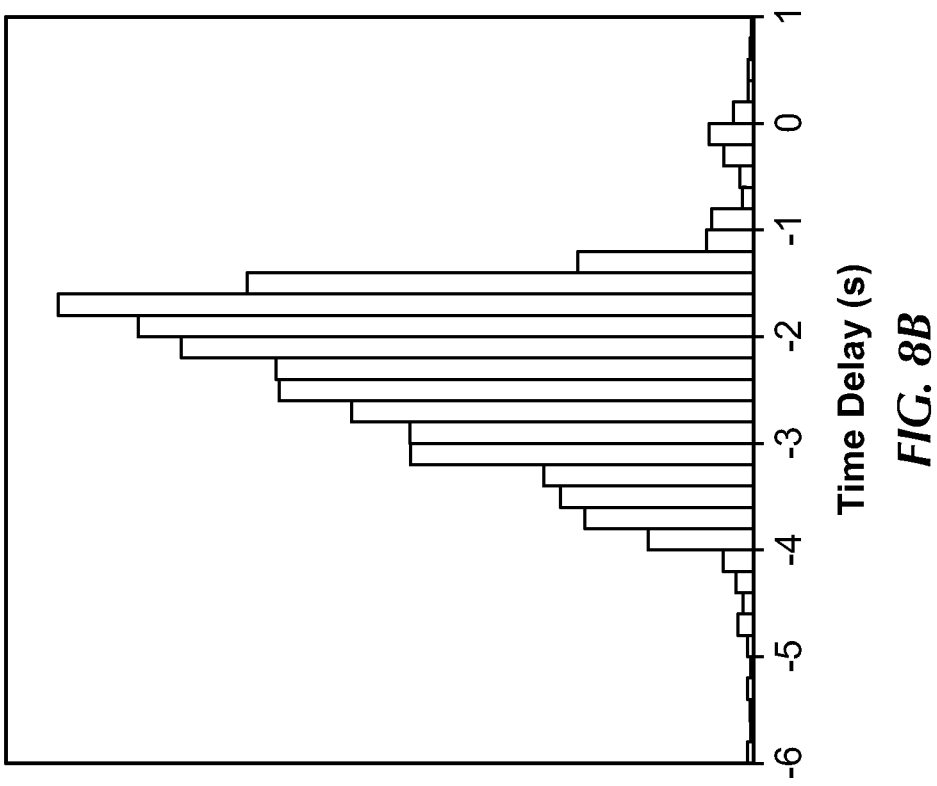
FIG. 8A is a chart illustrating a distribution of the transmission coefficient according to one embodiment.
Figure 8B:
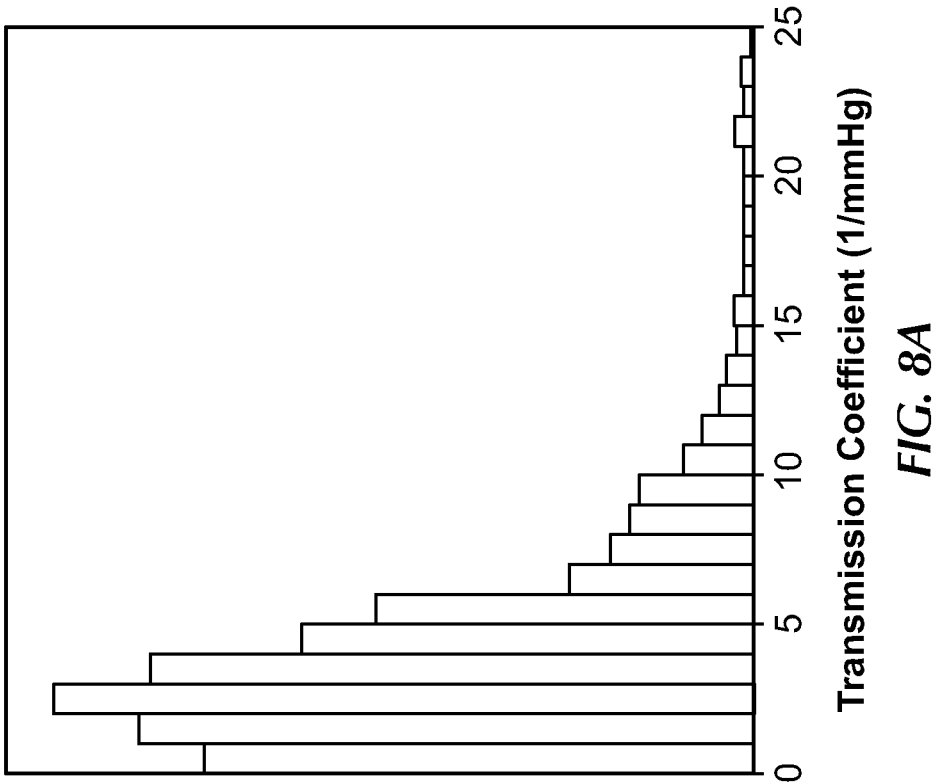
FIG. 8B is a chart illustrating a distribution of a time delay between oscillatory changes in pulse pressure and mean pressure at a respiratory frequency according to one embodiment.

FIG. 8A illustrates the distribution of the transmission coefficient, which quantifies the transmission of oscillatory changes in mean pressure at the respiratory frequency into oscillatory changes in pulse pressure. FIG. 8B illustrates the distribution of the time delay between oscillatory changes in pulse pressure and mean pressure at the respiratory frequency.

Figure 9:
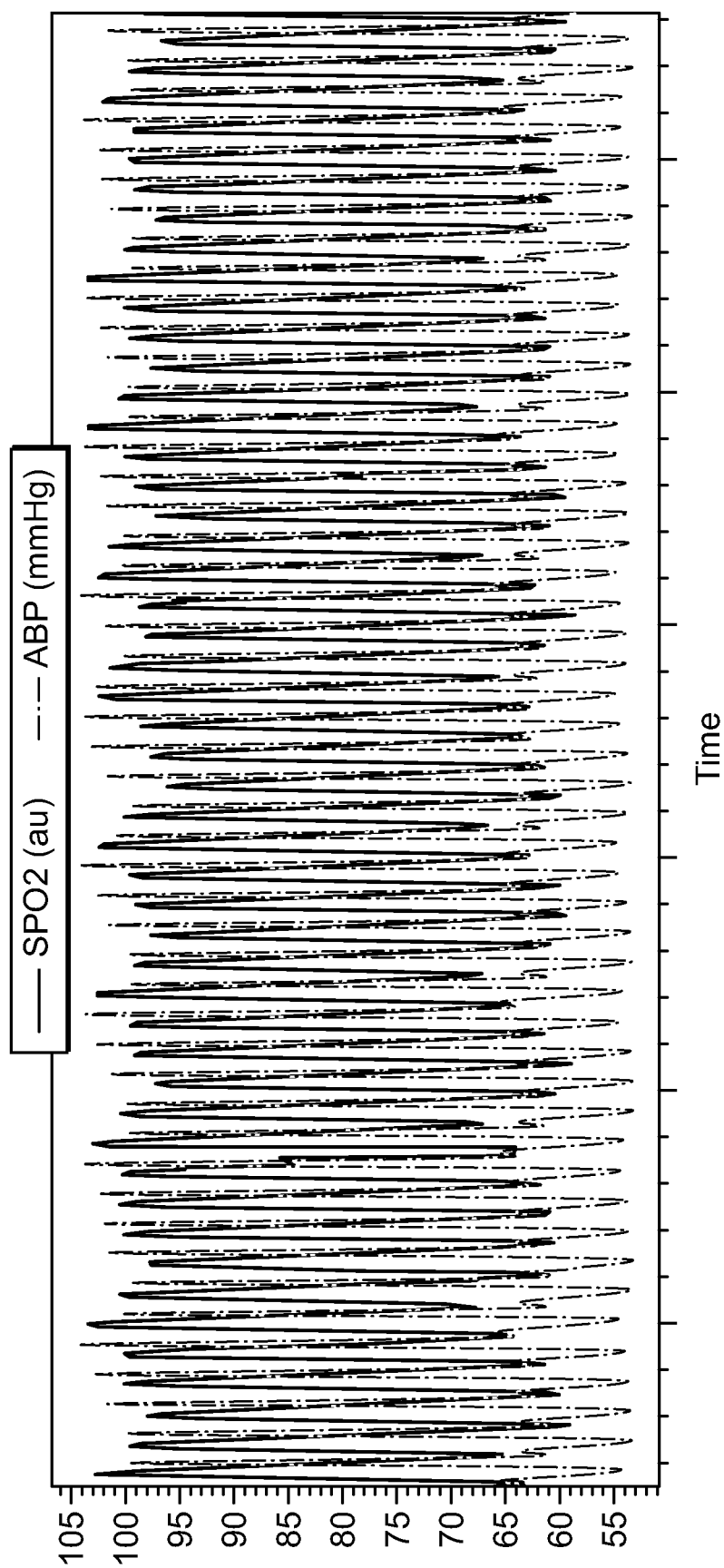
FIG. 9 is a graph illustrating a comparison between blood oxygen saturation and a blood pressure signal used for calculating PPV according to one embodiment.
Figure 10:
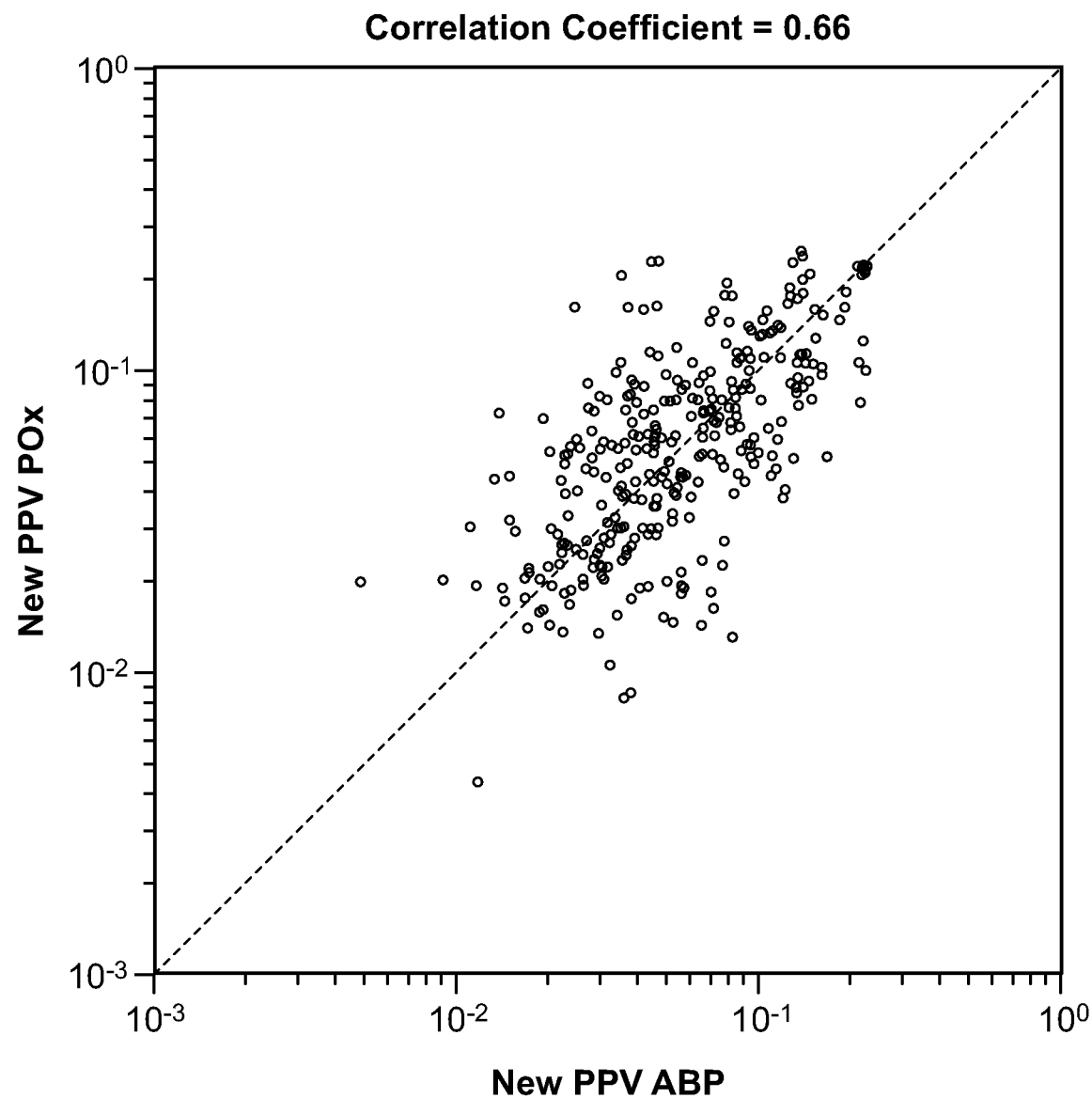
FIG. 10 is a graph illustrating a parity plot using a proposed technique for estimating PPV according to one embodiment on both arterial blood pressure and blood oxygen saturation.

While the technique described above was first developed using invasive measurements of arterial blood pressure, there is no theoretical restriction against using this technique on other related physiologic quantities to achieve the results. For example, in addition to arterial blood pressure measurements, other types of blood pressure measurements, such as venous, left and right atrial pulmonary, etc. could be used. Other types of real-time blood measurements can be used, such as blood flow velocity, volume, density, or concentration of blood components data. For example, a real-time continuous measurement of hemoglobin concentration can be used. From a clinical perspective, it would be highly advantageous to have the ability to accurately determine the fluid responsiveness of a patient who is breathing spontaneously, in a non-invasive way (a continuous blood pressure signal is invasive as it requires placement of a central line). As a result, the technique described above was applied to waveform measurements of blood oxygen saturation (SpO2), a continuous and non-invasive signal that is commonly available in critical care settings where knowledge of the fluid responsiveness state is valuable. Since the change in blood oxygen saturation varies along with the cardiac cycle, this signal also produces a waveform that contains both the cardiac signal, as well as a signal that is proportional to the respiratory cycle. The comparison between the SpO2 signal and the blood pressure signal used for calculating PPV can be seen in FIG. 9. From the figure, it is clear that both a change in the pulse pressure exists for both the blood pressure signal as well as the SpO2 signal. Since our technique simply looks at the relationship between cardiac cycle power, respiratory cycle power, and the convolved power between the two in a normalized way, our technique can be applied to the non-invasive SpO2 waveform signal to provide an estimate of the PPV, which can be used to assess fluid responsiveness. FIG. 10 is a parity plot using our PPV technique on both ABP and SpO2. As illustrated in FIG. 10, there is a substantial correlation between the results for each of the measurement modalities. This correlation was obtained across 3 orders of magnitude for the PPV signal for 57 patients subjected to 100 fluid boluses of saline solution. This indicates that the technique that described above for ABP measurements also performs well for estimating PPV using real-time non-invasive physiological measurements of blood oxygen saturation and other physiological data, including, but not limited to, pulse oximetry, near-infrared reflectance spectroscopy, doppler, etc. As a result, the development of our technique yields a means of accurately assessing PPV, and consequently fluid responsiveness, in patients who are spontaneously breathing in a completely non-invasive way. To our knowledge, this has never been demonstrated in human subjects as the tidal volume of a spontaneously breathing patient was always found to have too small of a signal relative to the noise of the patient to be effective with previous techniques In one embodiment, the proposed technique to measure pulse pressure variability over the respiratory cycle is based on Fourier analysis of the arterial pressure waveform. In the Fourier domain, there are three frequency bands of interest. These are the cardiac frequency (or heart rate HR), the respiratory frequency (or respiratory rate RR) and the frequency band associated with the cardio-respiratory interaction. The mathematical analysis shows that this latter frequency band resides in the vicinity of (HR+RR) and (HR−RR). Therefore, in the Fourier domain, it is possible to isolate the oscillatory components from each other and from unwanted components such as noise.

The specific equations set forth herein are illustrative and by way of example only, and other equations may be employed. Other mathematically equivalent analysis to measure aspects of the signal components located at HR+RR and HR−RR (and their associated higher harmonics) may be used. Because of the equivalence between time and frequency domain techniques, analogous time domain techniques can be used instead of the frequency domain techniques described above to achieve the same purpose.

The new technique takes into account the respiratory influence on the cardiac performance by using the mathematical structure of the oscillatory model (2). This particular structure is sought in the measured data once this data is Fourier-transformed. Specifically, the new technique looks for convolved components of cardiac and respiratory oscillations in the proper frequency bands in consistency with the mathematical model (2). Since random noise does not conform to this particular convolution structure, then the noise is removed. As a result, the new technique performs robustly in the presence of high levels of noise. The results displayed FIGS. 3 and 4 compare the performance and robustness of the new and old techniques. The signal-to-noise ratios at which each technique begins to lose accuracy are different. The new technique remains robust at signal-to-noise ratios approximately 6 times smaller than the old technique. This is a significant achievement for the application of PPV to recognize fluid responsiveness during spontaneous breathing and low tidal volume mechanical ventilation where the signal-to-noise ratio is expected to be small.

Additional signal processing and filtering techniques known to the art may be performed as desired to reject noise and artifacts that may potentially corrupt the Fourier transform and convolution analysis described herein.

Figure 11:
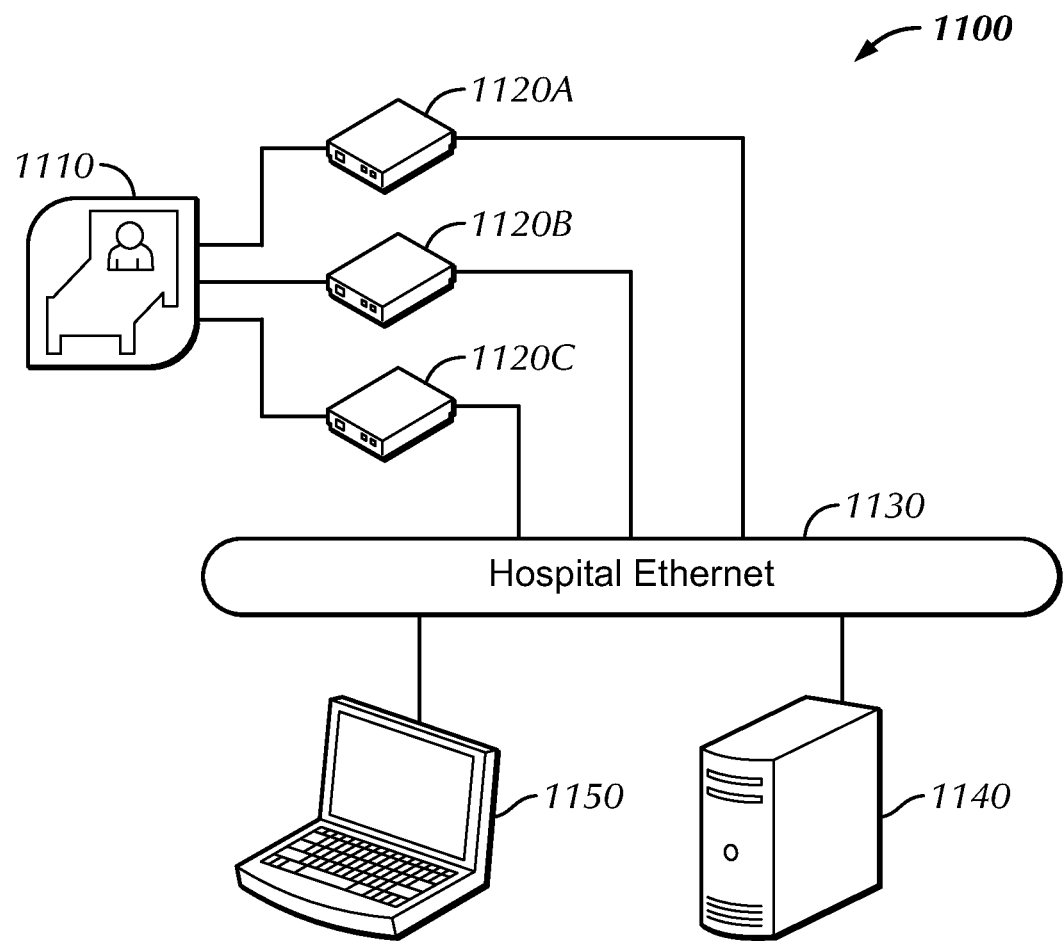
FIG. 11 is a block diagram illustrating a physiological monitoring system according to one embodiment.

FIG. 11 is a block diagram that illustrates a physiological monitoring system 1100 in which the techniques described above may be deployed. A patient 1110, such as a patient in an ICU is connected to one or more physiological sensors 1120A-C, which may be any desired type of sensor. These sensors 1120A-C may then be connected, directly or through intermediary devices, to a hospital network such as the hospital Ethernet 1130 illustrated in FIG. 11. Any type of data connection, wired or wireless, may be used. In one embodiment, a server 1140 collects the patient physiological data continuously in real time, and calculates a real time PPV estimate value. The PPV estimate may then be transmitted to a clinical display such as the laptop 1150. The elements illustrated in FIG. 10 are illustrative and by way of example only. Other devices, and connections between the devices may be used. In some embodiments, the server 1140 may provide storage for the physiological data and the calculated PPV estimate for historical, quality, or clinical research studies or any other desired purpose, for example. Although shown as a single network, any number of interconnected networks may be employed for the system 1100, and any number of the indicated devices may be deployed. Although illustrated for a single patient for clarity, implementations may deploy the elements of the system 1100 for all or any desired portion of the beds of the implementing facility. Some of the elements of the system 1100 may be remote from the clinical facility where the patients are monitored. Software for performing the techniques described herein may be stored as instructions on a computer readable medium. When executed the instructions cause the server 1140 to perform the actions. The computer readable medium may be any non-transitory type of medium, including, without limitation, memory circuitry, optical media, magnetic media, etc. The server 1140 may be any type of programmable device capable of performing the actions described here, whether or not called a server.

In addition to generating a prediction for PPV, the techniques described herein can be combined with other types of vital signs or physiologic features such as heart rate, respiration rate, oxygen saturation, blood pressure, central venous pressure, etc. to improve the predictive power of the PPV prediction. and generate a prediction of the fluid responsiveness of the patient. an increased cardiac output due to fluid resuscitation, bolus, or infusion. The combination may employ a regression model or other types of machine learning models based to generate such a prediction.

Although generally described herein as deployed in a clinical setting such as in an intensive care unit of a hospital, the system and techniques described may be implemented in other settings, including home monitoring settings. In a home monitoring setting, home measuring devices, measuring the same things as intensive care unit monitoring devices, are deployed and connected to a network for delivery of the data to the server 1040.

Figure 12:
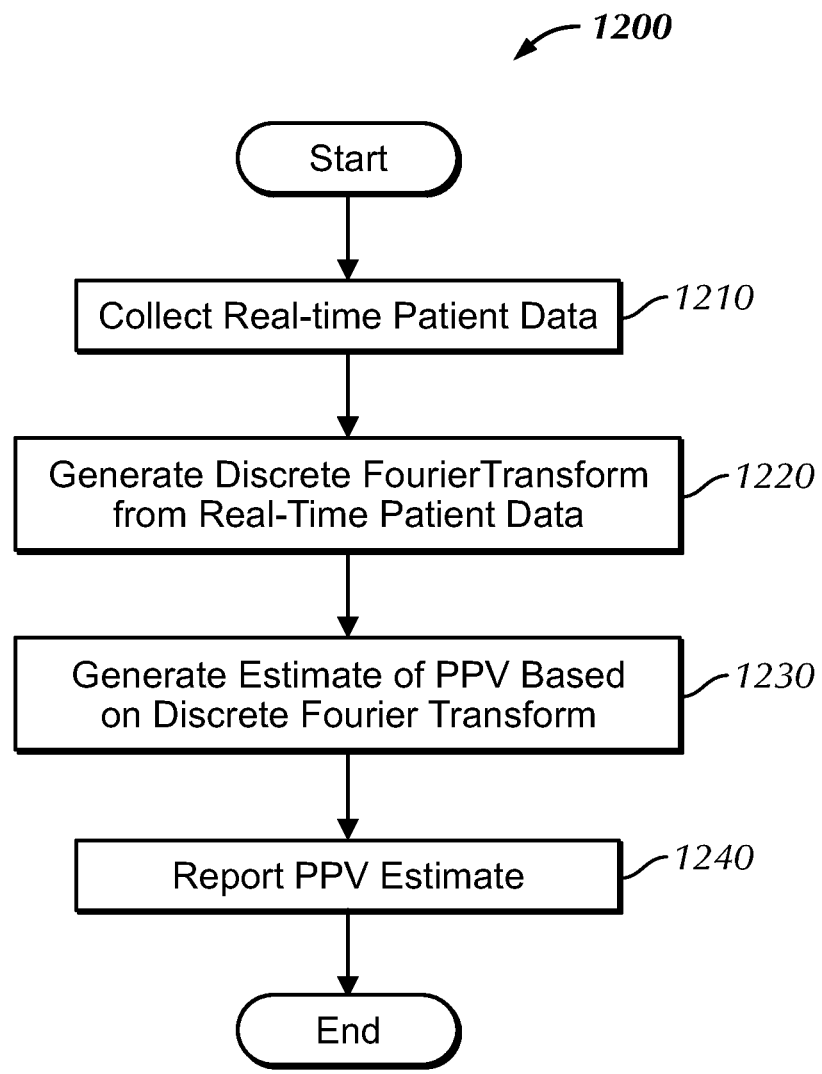
FIG. 12 is a flowchart illustrating a technique for predicting PPV according to one embodiment.

FIG. 12 is a flowchart illustrating a technique 1200 for generating a PPV estimate according to one embodiment. In block 1210, real time patient physiological data is collected continuously by a patient data monitoring system from one or more patient physiological sensors, typically attached to the patent. Any type of physiological sensor may be used, generating any type of waveform or data indicating the physiological condition corresponding to the sensor. A sensor may in some situations generate more than one type of physiological data. The sensor data is transmitted across one or more networks to a collecting computer, possibly through intermediary devices and networks. The collecting computer may store the collected real time physiological data in any desired way.

In block 1220, a discrete Fourier transform is generated as described above from the real time patient physiological data.

In block 1230, the discrete Fourier transform is used to generate a PPV estimate as described above.

In block 1240, the PPV estimate may be displayed, typically on a monitor screen of a clinical monitoring system that also displays patient physiological data, which may or may not be the same patient physiological data that is used to generate the clinical metric. The display of the clinical metric may be performed in any desired way, including numerical, graphical, or textual displays. In a non-clinical setting, such as a home monitoring system, the clinical metric may be displayed on a home monitor, in addition to or instead of a clinical monitoring system.

The actions of blocks 1210-1240 may be performed continuously as long as the patient is in the facility and is considered at risk, which may be the entire time the patient is in the facility. Although indicated as sequential actions in the flowchart, the actions indicated by the various blocks may be performed asynchronously in one embodiment, for example allowing the patient data collection of block 1210 to be performed continuously while the PPV estimate is being generated and displayed.

Because fluid resuscitation is an emergency technique in which time of care is of the essence, quickly and accurately determining fluid responsiveness can mean a difference between life and death for patients. Thus, the ability to take real-time measurements and predict fluid responsiveness in a patient such as provided by the proposed technique is critical. The proposed technique cannot be performed mentally or with pencil and paper in a clinically useful time, but requires the computational speed of a computer or other programmable device to guide the clinician in the proper treatment of the critically ill patient.

The above description is intended to be illustrative, and not restrictive. For example, the above-described embodiments may be used in combination with each other. Many other embodiments will be apparent to those of skill in the art upon reviewing the above description. The scope of the invention therefore should be determined with reference to the appended claims, along with the full scope of equivalents to which such claims are entitled.

We claim:

1. A method of predicting fluid responsiveness in a critically ill patient, comprising:
    measuring a heart rate (HR) and a respiration rate (RR) of the patient;
    measuring a real-time physiological data of the patient, including a real-time blood measurement data or a real-time blood oxygen saturation measurement data producing a real-time physiological waveform;
    performing a discrete Fourier transform of the real-time physiological waveform;
    generating an estimate of pulse pressure variability from the discrete Fourier transform of the real-time physiological waveform, based on HR−RR and HR+RR;
    displaying the estimate of pulse pressure variability on a clinical display; and
    administering fluid to the patient responsive to the estimate of pulse pressure variability exceeding a threshold that predicts fluid responsiveness of the patient.

2. The method of claim 1, further comprising:
    using signal processing and filtering to reject noise and artifacts in the real-time physiological data.

3. The method of claim 1, further comprising:
    generating a prediction of increased cardiac output due to fluid resuscitation by combining the estimate of pulse pressure variability with other vital signs data.

4. The method of claim 1, wherein performing the discrete Fourier transform of the real-time physiological waveform comprises:
    performing the discrete Fourier transform using frequencies based on a sampling frequency of the real-time physiological data.

5. The method of claim 1, wherein performing the discrete Fourier transform of the real-time physiological waveform comprises:
    calculating an amplitude of a respiratory component of the real-time physiological waveform of the measured real-time physiological data; and
    calculating a transmission coefficient corresponding to the respiratory component.

6. The method of claim 1, wherein performing the discrete Fourier transform of the real-time physiological waveform comprises:
    calculating a time delay between oscillatory changes in pulse pressure and mean pressure at a respiratory frequency.

7. The method of claim 1, wherein performing the discrete Fourier transform of the real-time physiological waveform comprises:
    fitting a transmission coefficient corresponding to a respiratory component of the real-time physiological waveform of the measured real-time physiological data and a time delay between oscillatory changes in pulse pressure and mean pressure at a respiratory frequency to measured discrete Fourier transform data.

8. A non-transitory machine-readable medium, on which are stored instructions for predicting fluid responsiveness in a critically ill patient, comprising instructions that when executed cause a programmable device to:
    measure a heart rate (HR) and a respiration rate (RR) of the patient;
    measure a real-time physiological data of the patient, including a real-time blood measurement data or a real-time blood oxygen saturation measurement data, producing a real-time physiological waveform;
    perform a discrete Fourier transform of the real-time physiological waveform;
    generate an estimate of pulse pressure variability from the discrete Fourier transform of the real-time physiological waveform, based on HR−RR and HR+RR;
    display the estimate of pulse pressure variability on a clinical display; and
    advise clinical personnel regarding whether to perform fluid resuscitation based on the estimate of pulse pressure variability.

9. The non-transitory machine-readable medium of claim 8, wherein the instructions further comprise instructions that when executed cause the programmable device to:
    use signal processing and filtering to reject noise and artifacts in the real-time physiological data.

10. The non-transitory machine-readable medium of claim 8, wherein the instructions further comprise instructions that when executed cause the programmable device to:
    generate a prediction of increased cardiac output due to fluid resuscitation by combining the estimate of pulse pressure variability with other vital signs data.

11. The non-transitory machine-readable medium of claim 8, wherein the instructions that when executed cause the programmable device to perform the discrete Fourier transform of the real-time physiological waveform comprise instructions that when executed cause the programmable device to:
    perform the discrete Fourier transform using frequencies based on a sampling frequency of the real-time physiological data.

12. The non-transitory machine-readable medium of claim 8, wherein the instructions that when executed cause the programmable device to perform the discrete Fourier transform of the real-time physiological waveform comprise instructions that when executed cause the programmable device to:
    calculate an amplitude of a respiratory component of the real-time physiological waveform of the measured real-time physiological data; and
    calculate a transmission coefficient corresponding to the respiratory component.

13. The non-transitory machine-readable medium of claim 8, wherein the instructions that when executed cause the programmable device to perform the discrete Fourier transform of the real-time physiological waveform comprise instructions that when executed cause the programmable device to:
    calculate a time delay between oscillatory changes in pulse pressure and mean pressure at a respiratory frequency.

14. The non-transitory machine-readable medium of claim 8, wherein the instructions that when executed cause the programmable device to perform the discrete Fourier transform of the real-time physiological waveform comprise instructions that when executed cause the programmable device to:
    fit a transmission coefficient corresponding to a respiratory component of the real-time physiological waveform of the measured real-time physiological data and a time delay between oscillatory changes in pulse pressure and mean pressure at a respiratory frequency to measured discrete Fourier transform data.

15. A physiological monitoring system, comprising:
    a programmable device;
    a storage medium, coupled to the programmable device, on which are stored instructions for predicting fluid responsiveness in a critically ill patient, comprising instructions that when executed cause the programmable device to:
measure a heart rate (HR) and a respiration rate (RR) of the patient;
measure a real-time physiological data of the patient, including a real-time blood measurement data or a real-time blood oxygen saturation measurement data, producing a real-time physiological waveform;
perform a discrete Fourier transform of the real-time physiological waveform;
generate an estimate of pulse pressure variability from the discrete Fourier transform of the real-time physiological waveform, based on HR−RR and HR+RR;
display the estimate of pulse pressure variability on a clinical display; and
advise clinical personnel regarding whether to perform fluid resuscitation based on the estimate of pulse pressure variability.

16. The physiological monitoring system of claim 15, wherein the instructions further comprise instructions that when executed cause the programmable device to:
generate a prediction of increased cardiac output due to fluid resuscitation by combining the estimate of pulse pressure variability with other vital signs data.

* * * * *